US012751662B2

(12) United States Patent
Jung et al.

(10) Patent No.: US 12,751,662 B2
(45) Date of Patent: Oct. 6, 2026

(54) METHOD FOR EVALUATING POSSIBILITY OF DYSPHAGIA BY ANALYZING ACOUSTIC SIGNALS, AND SERVER AND NON-TRANSITORY COMPUTER-READABLE RECORDING MEDIUM PERFORMING SAME

(71) Applicant: DAIN TECHNOLOGY, INC., Seoul (KR)

(72) Inventors: Ji Young Jung, Yongin-si (KR); Jee Young Song, Seoul (KR)

(73) Assignee: DAIN TECHNOLOGY, INC., Seoul (KR)

( * ) Notice: Subject to any disclaimer, the term of this patent is extended or adjusted under 35 U.S.C. 154(b) by 0 days.

(21) Appl. No.: 18/294,749

(22) PCT Filed: Aug. 2, 2022

(86) PCT No.: PCT/KR2022/011423

§ 371 (c)(1),
(2) Date: Feb. 2, 2024

(87) PCT Pub. No.: WO2023/014063

PCT Pub. Date: Feb. 9, 2023

(65) Prior Publication Data

US 2024/0341672 A1 Oct. 17, 2024

(51) Int. Cl.

*A61B 5/00* (2006.01)
*A61B 5/08* (2006.01)
(Continued)

(52) U.S. Cl.

CPC .......... *A61B 5/4205* (2013.01); *A61B 5/0823* (2013.01); *A61B 5/7267* (2013.01);
(Continued)

(58) Field of Classification Search

CPC ... A61B 5/4205; A61B 5/7267; A61B 5/7282; A61B 7/003; G16H 50/20; G10L 15/04;
(Continued)

(56) References Cited

U.S. PATENT DOCUMENTS

2012/0071777 A1 3/2012 MacAuslan
2020/0015709 A1 * 1/2020 Peltonen ................ G06N 3/045
(Continued)

FOREIGN PATENT DOCUMENTS

KR 1020140142330 A 12/2014
KR 1020200119414 A 10/2020
(Continued)

OTHER PUBLICATIONS

Morice, A. H., et al. “ERS guidelines on the assessment of cough.” European respiratory journal 29.6 (2007): 1256-1276 (Year: 2007).*
(Continued)

*Primary Examiner* — Bhavesh M Mehta
*Assistant Examiner* — Joseph J. Yamamoto
(74) *Attorney, Agent, or Firm* — Dinsmore & Shohl LLP; Yongsok Choi, Esq.

(57) ABSTRACT

According to one embodiment of the present disclosure, an audio analysis method for determining the possibility of dysphagia may be provided, the method comprising the steps of: obtaining audio signals; sorting out a cough signal from among the audio signals; identifying the presence and/or intensity of an explosive phase in the cough signal; and determining that there is a possibility of dysphagia if there is no explosive phase in the cough signal or if the intensity of the explosive phase is weak even if there is an explosive phase.

6 Claims, 13 Drawing Sheets

(51) Int. Cl.

| | |
|---|---|
| ***A61B 7/00*** | (2006.01) |
| ***G10L 15/04*** | (2013.01) |
| ***G10L 15/06*** | (2013.01) |
| ***G10L 25/18*** | (2013.01) |
| ***G10L 25/21*** | (2013.01) |
| ***G10L 25/66*** | (2013.01) |
| ***G16H 50/20*** | (2018.01) |

(52) U.S. Cl.
CPC ............ *A61B 5/7282* (2013.01); *A61B 7/003* (2013.01); *G10L 15/04* (2013.01); *G10L 15/063* (2013.01); *G10L 25/18* (2013.01); *G10L 25/21* (2013.01); *G10L 25/66* (2013.01); *G16H 50/20* (2018.01)

(58) Field of Classification Search
CPC ....... G10L 15/063; G10L 25/18; G10L 25/21; G10L 25/66
See application file for complete search history.

(56) References Cited

U.S. PATENT DOCUMENTS

2022/0277764 A1* 9/2022 Ciliberti ................ G16H 10/60
2022/0338756 A1* 10/2022 Dzhekiev ............... G10L 25/18

FOREIGN PATENT DOCUMENTS

KR 1020200122301 A 10/2020
KR 102216160 B1 2/2021

OTHER PUBLICATIONS

Nishino, Takashi. "The swallowing reflex and its significance as an airway defensive reflex." Frontiers in physiology 3 (2013): 489 (Year: 2013).*
International Search Report of PCT-KR2022-011423 dated Nov. 11, 2022.
Written Opinion of PCT-KR2022-011423 dated Nov. 11, 2022.

* cited by examiner

METHOD FOR EVALUATING POSSIBILITY OF DYSPHAGIA BY ANALYZING ACOUSTIC SIGNALS, AND SERVER AND NON-TRANSITORY COMPUTER-READABLE RECORDING MEDIUM PERFORMING SAME

TECHNICAL FIELD

The present disclosure relates to a method for determining a possibility of dysphagia by analyzing audio signals and, particularly, to a method for determining whether a subject has a possibility of suffering from dysphagia by recording voices of the subject and analyzing features of the recorded audio signals.

BACKGROUND ART

Swallowing food is referred to as deglutition, which is achieved by various organs such as the oral cavity, the pharynx, and the esophagus that move in an organic and harmonious manner. Dysphagia or difficulty in swallowing food refers to a condition in which such organic movements are disrupted for some reason and the food is unable to be swallowed, or the food passes into the respiratory tract of a person. For example, dysphagia has symptoms including: a case where mechanical narrowing of the pharynx or larynx occurs; a case where difficulty in swallowing occurs due to a disorder (i.e., pseudobulbar paralysis) of motor cranial nerve nuclei (i.e., facial nerves, vagus nerves, hypoglossal nerves) involved in the lips, the tongue, the palate, the pharynx, and the larynx; and a case where discomfort occurs in swallowing due to a disorder occurring in the oral cavity area, a pharynx area, or an esophagus area.

Meanwhile, even when a patient is suffering from dysphagia, the symptoms may be mild or unrecognized, so the dysphagia is not diagnosed early and is neglected, resulting in that food is aspirated into the lungs, whereby patients often go to the hospital only when their pneumonia and the like become more severe. In addition, since patients who frequently develop dysphagia are generally elderly, when complications such as pneumonia occur, inflammatory response also becomes more severe, thereby becoming a factor as well that greatly worsens health.

In the present disclosure, a method of detecting whether dysphagia occurs or not and/or severity thereof at an early stage will be described in order to prevent the above-described problems in advance.

DISCLOSURE

Technical Problem

An objective of the present disclosure to solve the problems is to provide a method for determining a possibility of dysphagia by analyzing an audio signal.

Another objective of the present disclosure to solve the problems is to provide a method for determining a possibility of dysphagia by analyzing a cough signal.

A yet another objective of the present disclosure to solve the problems is to provide a method for determining a possibility of dysphagia by extracting a cough signal from an audio signal and analyzing the extracted cough signal.

A still another objective of the present disclosure to solve the problems is to provide a method for determining a possibility of dysphagia by dividing a cough signal into specific sections and using feature values of the specific sections divided.

A still another objective of the present disclosure to solve the problems is to provide a method of monitoring a condition of dysphagia by analyzing an audio signal.

A still another objective of the present disclosure to solve the problems is to provide a method of analyzing an audio signal so as to determine whether an emergency situation has occurred or not.

The problems to be solved in the present disclosure is not limited to the above-described problems, and the problems not described herein will be clearly understood by those skilled in the art to which the embodiments of the present disclosure belong from the present disclosure and accompanying drawings.

Technical Solution

According to one embodiment of the present disclosure, there is provided an audio analysis method for providing information on dysphagia, the audio analysis method including: obtaining an audio signal by using an electronic device; obtaining candidate cough signals from the audio signal, each of the candidate cough signals comprising an onset signal and having a preset length; obtaining at least one cough signal from the candidate cough signals; and determining whether an explosive phase exists in the at least one cough signal by using a phase classification model, wherein the phase classification model is trained with at least a first training data set and a second training data set, the first training data set comprises data based on a first cough signal and data indicating that there is the explosive phase, the second training data set comprises data based on a second cough signal and data indicating that there is no explosive phase, and a frequency band of a signal corresponding to a preset time period from a start point of the first cough signal in the first cough signal is higher than a frequency band of a signal corresponding to the preset time period from a start point of the second cough signal in the second cough signal.

The problem solutions of the present disclosure are not limited to the above-described solutions, and solutions that are not mentioned may be understood clearly to those skilled in the art to which the embodiments of the present disclosure belong from the present disclosure and the accompanying drawings.

Advantageous Effects

According to an exemplary embodiment of the present disclosure, a possibility of dysphagia may be determined relatively easily.

According to the exemplary embodiment of the present disclosure, a possibility of dysphagia may be determined by using only a cough signal.

According to the exemplary embodiment of the present disclosure, a possibility of dysphagia may be determined by analyzing sounds generated from a user during an arbitrary time period.

According to the exemplary embodiment of the present disclosure, whether a user has an emergency situation or not may be checked in real time.

The effects according to the present disclosure are not limited to the above-described effects, and the effects not mentioned herein may be clearly understood by those skilled in the art to which the embodiments of the present disclosure belong from the present disclosure and accompanying drawings.

BEST MODE

Figure 1:
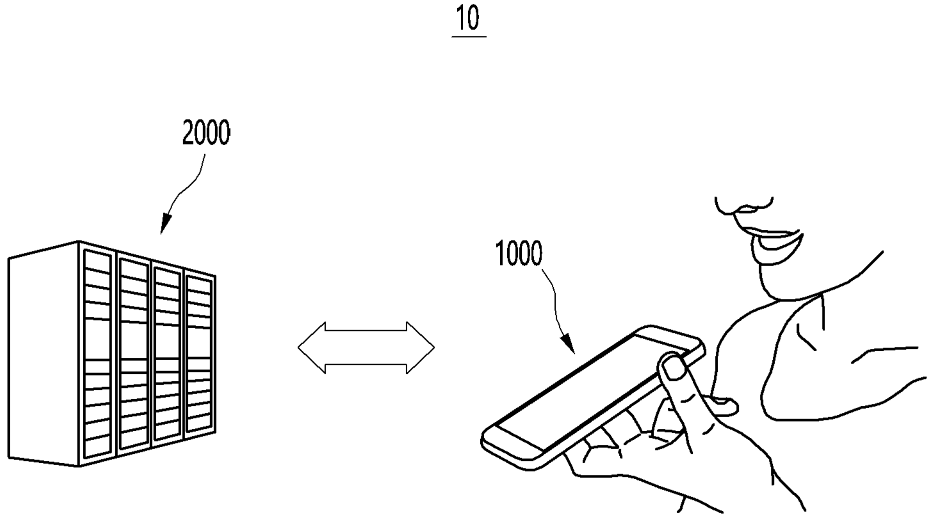
FIG. 1 is a view illustrating a configuration of an audio analysis system according to an exemplary embodiment of the present disclosure.

According to an exemplary embodiment of the present disclosure, there is provided an audio analysis method for providing information on dysphagia, the audio analysis method including: obtaining an audio signal by using an electronic device; obtaining candidate cough signals from the audio signal, each of the candidate cough signals including an onset signal and having a preset length; obtaining at least one cough signal from the candidate cough signals; and determining whether an explosive phase exists in the at least one cough signal by using a phase classification model, wherein the phase classification model is trained with at least a first training data set and a second training data set, the first training data set includes data based on a first cough signal and data indicating that there is the explosive phase, the second training data set includes data based on a second cough signal and data indicating that there is no explosive phase, and a frequency band of a signal corresponding to a preset time period from a start point of the first cough signal in the first cough signal is higher than a frequency band of a signal corresponding to the preset time period from a start point of the second cough signal in the second cough signal.

The audio analysis method further includes determining that there is a possibility of the dysphagia when no explosive phase exists in the cough signal.

The audio analysis method further includes: obtaining an intensity value of the explosive phase of the cough signal when the explosive phase exists in the cough signal; and determining that there is a possibility of the dysphagia when the intensity value is less than or equal to a preset value.

The determining of whether the explosive phase exists is performed for a plurality of cough signals, the audio analysis method further includes determining that there is a possibility of the dysphagia when a ratio of cough signals in which the explosive phase exists among the plurality of cough signals is greater than or equal to a preset value.

The obtaining of the at least one cough signal from the candidate cough signals includes determining whether each of the candidate cough signals is a cough or not by using a cough determination model, the cough determination model is trained with at least a first cough training data set and a second cough training data set, the first cough training data set includes data based on a third cough signal and data indicating the cough signal, and the second cough training data set includes data based on a fourth cough signal and data indicating not the cough signal.

According to another exemplary embodiment of the present disclosure, there is provided an audio analysis method for providing information on dysphagia, the audio analysis method including: outputting a guide so as to induce voluntary coughing of a user by using an electronic device; obtaining a cough signal by recording a sound generated by the user by using the electronic device; dividing the cough signal into a first time section starting from a start point of the cough signal and a second time section after the first time section; and determining a possibility of the dysphagia of the user by analyzing a first signal corresponding to the first time section in the cough signal.

The determining of the possibility of the dysphagia of the user includes: obtaining a root mean square (RMS) value of a specific frequency band of the first signal; and determining that there is the possibility of the dysphagia when the RMS value is less than or equal to a preset value.

The determining of the possibility of the dysphagia of the user includes: obtaining a ratio of the RMS value of the specific frequency band to an RMS value of an entire frequency band of the first signal; and determining that there is the possibility of the dysphagia when the ratio is less than or equal to a preset ratio value.

According to a yet another exemplary embodiment of the present disclosure, there is provided an audio analysis method for providing information on dysphagia, the audio analysis method including: outputting a guide to induce voluntary coughing of a user by using an electronic device; obtaining a cough signal by recording a sound generated by the user by using the electronic device; dividing the cough signal into a plurality of windows having a predetermined length and obtaining fragment cough signals corresponding to the plurality of respective windows; calculating feature values of the respective fragment cough signals; obtaining a representative fragment signal among the fragment cough signals on the basis of the feature values; and determining that there is a possibility of the dysphagia when a feature value of a predetermined frequency band compared to a feature value of an entire frequency band in the representative fragment signal is less than or equal to a preset threshold value.

The feature values to be calculated are RMS values, and the representative fragment signal is a fragment cough signal corresponding to the largest feature value among the calculated feature values.

MODE FOR INVENTION

The above-described objectives, features, and advantages of the present specification will become more apparent from the following detailed description in conjunction with the accompanying drawings. However, since the present specification may have various changes and may have various exemplary embodiments, specific exemplary embodiments will be exemplified in the drawings and described in detail below.

The same reference numbers throughout the specification indicate the same components, in principle. In addition, components having the same function within the scope of the same idea shown in the drawings of each exemplary embodiment will be described by using the same reference numerals, and a redundant description thereof will be omitted.

Numbers (e.g., first, second, etc.) used in a process of describing the present specification are merely identification symbols for distinguishing one component from other components.

In addition, the words "module" and "part/unit" used as noun suffixes for the components used in the following exemplary embodiments are given or mixed in consideration of merely the ease of writing the specification, and do not have distinct meanings or roles by themselves.

Unless specifically stated or clear from the context, a term "about" or "around" in reference to a numerical value may be understood to mean a stated numerical value and a value up to +/−10% of the numerical value. The term "about" or "around" in reference to a numerical range may be understood to mean a range from a value 10% lower than a lower limit of the numerical range to a value 10% higher than an upper limit of the numerical range.

In the exemplary embodiments below, the singular forms are intended to include the plural forms as well, unless the context clearly indicates otherwise.

In the following exemplary embodiments, terms such as "comprise", "include", or "have" mean that a feature or a component described in the specification exists, and the possibility that one or more other features or components may be added is not precluded.

In the drawings, the size of the components may be exaggerated or reduced for convenience of description. For example, the size and thickness of each component shown in the drawings or views are arbitrarily represented for convenience of description, and the embodiments of the present disclosure are not necessarily limited to the illustrated drawings or views.

Where certain exemplary embodiments are otherwise implementable, a specific process order may also be performed different from the described order. For example, two processes described in succession may be performed substantially and simultaneously, or may be performed in an order opposite to the described order.

In the following exemplary embodiments, when a film, a region, a component, and/or the like are connected to a target, this includes not only a case where the film, the region, and/or the component are directly connected to the target, but also a case where the film, the region, and/or the component are indirectly connected to the target by means of another film, another region, and/or another component that are interposed therebetween.

For example, in the present specification, when it is said that a film, a region, a component, and/or the like are electrically connected to a target, this includes not only a case where the film, the region, the component, and/or the like are directly and electrically connected to the target, but also a case where the film, the region, the component, and/or the like are indirectly and electrically connected to the target by means of another film, another region, another component, and/or the like that are interposed therebetween.

The research conducted for the present specification is the result of research conducted with support from the "International Joint Technology Development Project" of the Ministry of Trade, Industry and Energy and the Korea Institute for Advancement of Technology in South Korea (Project No. P0021550).

The present disclosure relates to a method for determining a possibility of dysphagia by analyzing an audio signal and, particularly, to a method for determining whether a subject has a possibility of suffering from dysphagia by recording voices of the subject and analyzing features of the recorded audio signal.

In the present disclosure, the audio signal may mean a signal obtained by recording a person's voices by using an electronic device to be described later. Each audio signal may have unique features, and may be expressed in various forms, such as expressed in a form of intensity based on time or expressed in a form of intensity based on frequency. Each audio signal has a form changeable depending on processing methods, and may include feature values reflected with unique characteristics for each form.

Accordingly, analyzing an audio signal may mean a process of finding unique features of the corresponding audio signal and obtaining desired information from the audio signal on the basis of the features.

In the present disclosure, determining a possibility of dysphagia may mean predicting the presence or absence of dysphagia, or predicting a probability of having dysphagia. Alternatively, the determining of the possibility of dysphagia may mean predicting severity (or seriousness) of the dysphagia. Furthermore, the determining of the possibility of dysphagia may mean obtaining and providing information on the presence/absence or severity of the dysphagia.

[Audio Analysis System]

Hereinafter, an audio analysis system 10 for determining a possibility of dysphagia by analyzing an audio signal will be described with reference to FIG. 1.

FIG. 1 is a view illustrating a configuration of the audio analysis system 10 according to the exemplary embodiment. Referring to FIG. 1, the audio analysis system 10 may include an electronic device 1000 and an audio analysis unit 2000.

The electronic device 1000 may record ambient sounds. The electronic device 1000 may obtain an audio signal by recording the ambient sounds.

The electronic device 1000 may provide the obtained audio signal to the audio analysis unit 2000. Through a built-in communication unit thereof, the electronic device 1000 may transmit the audio signal to the audio analysis unit 2000.

The sounds recorded through the electronic device 1000 may include voices of a person carrying the electronic device 1000.

According to the exemplary embodiment of the present disclosure, the electronic device 1000 may be set to record ambient sounds for a predetermined period of time. For example, a user may activate a recording function of the electronic device 1000 while eating food, and the electronic device 1000 may obtain an audio signal by recording sounds related to food consumption of the user. In this way, the electronic device 1000 may record sounds related to arbitrary movements or actions of the user.

According to the exemplary embodiment of the present disclosure, the electronic device 1000 may be used for the purpose of recording factitious sounds of a person. For example, a user may make voluntary coughing while activating the recording function of the electronic device 1000, so as to allow the electronic device 1000 to obtain an audio signal related to that coughing.

In this case, the electronic device 1000 may output a guide instructing to cough once or multiple times through an output means (e.g., a display panel, a speaker, etc.). For another example, a user may speak a specific word or sentence while activating the recording function of the electronic device 1000, so as to allow the electronic device 1000 to obtain an audio signal related to voices of the user. Even at this time, the electronic device 1000 may output a guide regarding the specific word or sentence to the user through the output means.

The electronic device 1000 may have various forms of use. For example, the user may activate the recording function in a state of placing the electronic device 1000 near the user. For another example, the user may activate the recording function in a state of placing the electronic device 1000 around or in contact with the neck of the user.

The electronic device 1000 may be implemented in various forms. For example, the electronic device 1000 may be implemented with a wearable device, which is equipped with a recording function, such as a smart watch, a smart band, a smart ring, and a smart neckless, and may also implemented with a smartphone, a tablet, a desktop, a laptop, a portable recorder, an installation-type recorder, or the like.

The electronic device 1000 may also be used as a means of transmitting information related to dysphagia to a user. For example, the electronic device 1000 may obtain information on a possibility of dysphagia from the audio analysis unit 2000 and output the information to the user.

The audio analysis unit 2000 may obtain an audio signal from the electronic device 1000.

The audio analysis unit 2000 may determine a possibility of dysphagia for the user by analyzing the audio signal. A process by which the audio analysis unit 2000 determines the possibility of dysphagia will be described in detail later.

The audio analysis unit 2000 may mean a program. The audio analysis unit 2000 may exist in a form saved on a server, a web server, or a non-transitory computer-readable recording medium.

Meanwhile, the electronic device 1000 and the audio analysis unit 2000 may be implemented as one device. For example, the audio analysis unit 2000 may obtain an audio signal by including a module having its own recording function. For another example, components of the audio analysis unit 2000 may be built into the electronic device 1000 and provide a function for the electronic device 1000 to analyze an audio signal on its own.

The audio analysis system 10 may additionally include an external server.

The external server may store or provide various data. For example, the external server may store an audio signal obtained from the electronic device 1000 or store dysphagia-related information obtained from the audio analysis unit 2000. For another example, the external server may provide an audio signal obtained from the electronic device 1000 to the audio analysis unit 2000 and provide dysphagia-related information obtained from the audio analysis unit 2000 to the electronic device 1000.

[Audio Analysis Unit]

Figure 2:
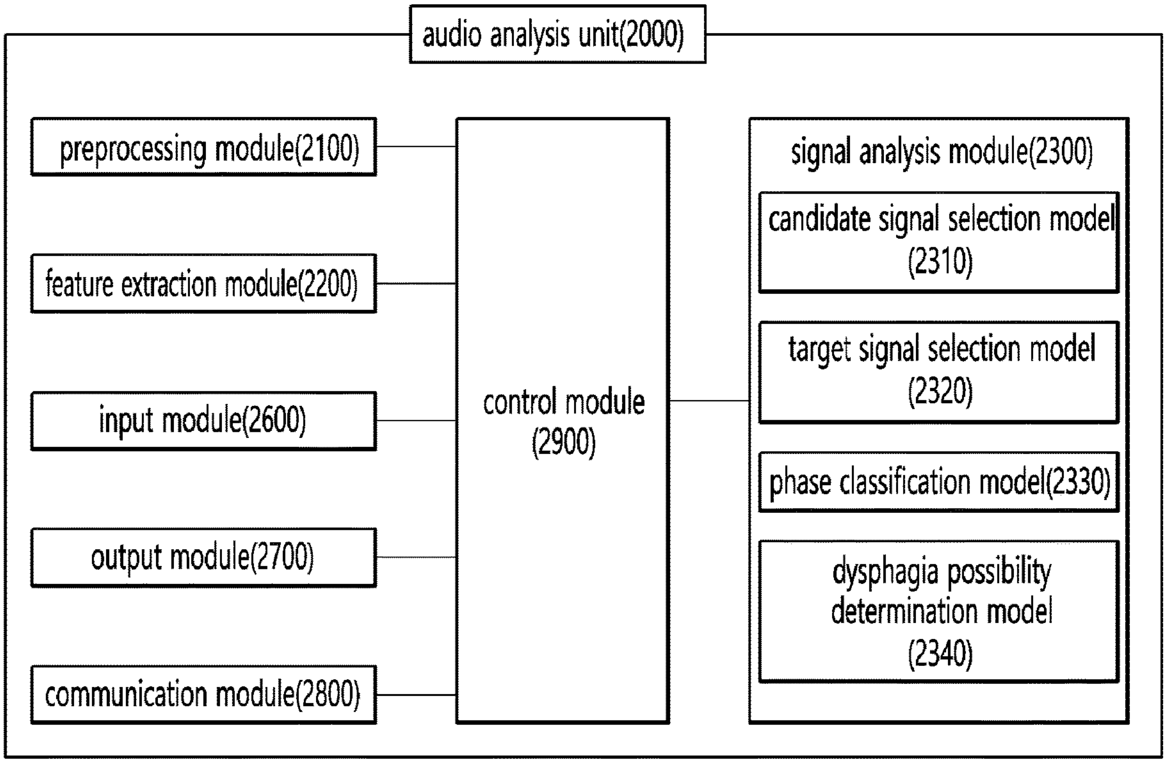
FIG. 2 is a view illustrating a configuration of an audio analysis unit constituting the audio analysis system according to the exemplary embodiment of the present disclosure.

FIG. 2 is a view illustrating a configuration of the audio analysis unit 2000 constituting the audio analysis system 10 according to the exemplary embodiment of the present disclosure.

The audio analysis unit 2000 may determine a possibility of dysphagia by analyzing an audio signal. Specifically, the audio analysis unit 2000 may output data indicating the possibility of dysphagia by using the audio signal. The output data may include: a value regarding presence or absence of dysphagia; a value regarding severity or seriousness of dysphagia; or a value regarding a possibility of dysphagia, and each value may be expressed as a probability value.

The audio analysis unit 2000 may include a preprocessing module 2100, a feature extraction module 2200, a signal analysis module 2300, an input module 2600, an output module 2700, a communication module 2800, and a control module 2900.

The preprocessing module 2100 may perform preprocessing on the audio signal received by the audio analysis unit 2000. The preprocessing may be understood as a process performed before extracting a feature value from the audio signal in the process of analyzing the audio signal.

In the preprocessing module 2100, filtering for removing noise maybe performed on the audio signal. Here, the filtering may mean a process of excluding noise-related data from the sound data, and to this end, a high-pass filter, a low-pass filter, a band-pass filter, and the like may be used. Filtering by the preprocessing module 2100 may also be omitted.

Meanwhile, in the preprocessing module 2100, windowing that will be described later may be performed.

The feature extraction module 2200 may extract a feature value from the audio signal or the preprocessed audio signal. Here, the feature value may mean numerical value obtained by quantifying unique features of the audio signal. For example, the feature value may include at least one of a time domain signal intensity value, a time domain root mean square (RMS) value, a time domain spectral magnitude value, a time domain energy value, time domain power value, a spectral centroid, a frequency domain spectral magnitude value, a frequency band RMS value, a frequency band energy value, a frequency band power value, a spectrogram magnitude value, a Mel-spectrogram magnitude value, a bispectrum score (BGS), a non-Gaussianity score (NGS), Formants Frequencies (FF), a Log Energy (LogE), a zero crossing rate (ZCR), a Kurtosis (Kurt), and a Mel-frequency cepstral coefficient (MFCC).

The feature extraction module 2200 may convert the preprocessed audio signal and extract an feature value therefrom. The feature extraction module 2200 may perform different types of transformation depending on the feature value to be extracted from the audio signal. For example, in a case where the feature value to be extracted is the spectral magnitude value, the feature extraction module 2200 may convert the preprocessed audio signal into either spectrum data having a frequency axis or spectrum data having a time axis. As another example, in a case where the feature value to be extracted is the Mel-spectrogram image value, the feature extraction module 2200 may convert the preprocessed audio signal into spectrogram image data having a time axis and a frequency axis. In a case of a plurality of types of the feature value to be extracted, the feature extraction module 2200 may convert the preprocessed audio signal into various types of data.

The signal analysis module 2300 may determine a possibility of dysphagia by using the features extracted from the audio signal. The signal analysis module 2300 may include a candidate signal selection model 2310, a target signal selection model 2320, a phase classification model 2330, and a dysphagia possibility determination model 2340.

The signal analysis module 2300 may obtain a characteristic of the audio signal or information required for determining a possibility of dysphagia by using the features extracted from the audio signal. In addition, the signal analysis module 2300 may output a result obtained by determining the possibility of dysphagia by using the characteristic of the audio signal or information required for determining the possibility of dysphagia.

A target signal to be analyzed may be obtained from the audio signal by using the candidate signal selection model 2310 and the target signal selection model 2320.

Here, the target signal may mean a signal required for determining a possibility of dysphagia. For example, the target signal may include a signal reflected with a user's physiological phenomena (e.g., coughing, cough by aspiration, clearing throat, sneezing, etc.), a signal related to the physiological phenomena, a signal determined to include sounds related to the physiological phenomena, etc. For another example, the target signal may include a signal corresponding to a time section including an onset point in the audio signal.

The target signal may mean a signal corresponding to a specific time section in the entire time section of the audio signal. Alternatively, the target signal may mean a signal corresponding to a specific frequency band in the entire frequency band of the audio signal.

Meanwhile, a process of selecting the target signal from the audio signal may include a process of first selecting a candidate signal from the audio signal.

The candidate signal may mean a signal questionable to be the target signal in the audio signal. The candidate signal extracted from the audio signal may become the target signal through additional analysis or determination. For example, in a case where the target signal is a cough signal, the candidate signal may be understood as a candidate cough signal questionable to be a cough-related signal in the audio signal.

Meanwhile, the candidate signal may also be used as the target signal without the additional analysis or determination.

The candidate signal selection model 2310 may obtain, as the candidate signal, a signal satisfying a preset condition in the audio signal. For example, by detecting an onset point, the candidate signal selection model 2310 may select the candidate signal in the audio signal. Specifically, the candidate signal selection model2310 may select, as the candidate signal, a signal corresponding to a time section including a time point where the onset point is detected and having a preset time interval. Here, the onset point refers to a portion where a rapid change occurs in the signal. The onset point may mean a point where a value related to signal strength such as a root mean square (RMS) value or a signal energy value, a value indicating a degree of change in a spectrum of the signal such as a spectral flux, or an average value thereof is greater than or equal to a threshold value, or a point where variance in signal intensity value or its average value within a predetermined period of time is greater than or equal to a threshold value. In addition, here, the preset time interval may be determined within 0.05 seconds to 2 seconds.

The candidate signal selection model2310 maybe used in a case where the audio analysis unit 2000 analyzes an audio signal recorded for an arbitrary time. For example, it is assumed that the audio analysis unit 2000 records sounds during a food intake process of a user, and determines a possibility of dysphagia by analyzing a cough signal that appear during the food intake process. In this case, it is required to selectively analyze a cough signal, a cough-by-aspiration signal, or a clearing-throat signal in the audio signal recorded during the entire food intake process. Here, when selecting a target signal to be analyzed, such as a cough signal, a cough-by-aspiration signal, or a clearing-throat signal, in the audio signal, the candidate signal selection model 2310 may be used in selecting a candidate signal questioned to be the target signal.

The candidate signal selection model2310 and the target signal selection model2320 may be omitted. For example, as described above, an audio signal obtained when user's voluntary coughing is recorded, or voices of the user saying a specific word or sentence are recorded may be used as the target signal.

The target signal selection model 2320 may select a target signal from a candidate signal. The target signal selection model 2320 may determine whether to use the candidate signal as the target signal by using a feature extracted from the candidate signal.

The target signal selection model 2320 may be implemented by using a deep-learning model or a rule-based machine learning model. The operation process or implementation method of the target signal selection model 2320 will be described later.

The phase classification model 2330 may divide a target signal to be analyzed into at least one section. For example, in a case where a target signal to be analyzed is a cough signal, the phase classification model 2330 may divide the cough signal into an explosive phase, an intermediate phase, and a voiced phase.

The phase classification model2330 maybe implemented by using a deep learning model or a rule-based machine learning model. The operation process or implementation method of the phase classification model 2330 will be described later.

The phase classification model 2330 may be omitted depending on the audio analysis method to be performed by the audio analysis unit 2000.

The dysphagia possibility determination model 2340 may calculate a value regarding a possibility of dysphagia. For example, in the case where a target signal to be analyzed is a cough signal, the dysphagia possibility determination model 2340 may output a possibility value indicating the possibility of dysphagia on the basis of the intensity or presence/absence of an explosive phase, and/or intensity or presence/absence of an voiced phase of the cough signal. For another example, in the case where a target signal to be analyzed is a cough signal, the dysphagia possibility determination model 2340 may output a value indicating the presence or absence of dysphagia on the basis of an RMS value for each unit of time section of the cough signal.

The dysphagia possibility determination model 2340 may be implemented by using a deep learning model or rule-based machine learning model. The operation process or implementation method of the dysphagia possibility determination model 2340 will be described later.

The input module 2600 may receive user input from a user. The user input may be made in various forms including a key input, a touch input, and a voice input. For example, in a comprehensive concept, the input module 2600 includes all not only traditional types of a keypad, a keyboard, and a mouse, but also touch sensors for detecting a user's touch, in addition to various types of input means for detecting or receiving various other types of user inputs.

The output module 2700 may output information on the possibility of dysphagia and provide the information to a user. In a comprehensive concept, the output module 2700 includes all of a display for outputting images, a speaker for outputting sounds, and a haptic device for generating vibrations, in addition to various other types of output means.

The communication module 2800 may communicate with an external device. The audio analysis unit 2000 may transmit and receive data to and from the electronic device 1000 or an external server through the communication module 2800. For example, the audio analysis unit 2000 may provide information related to dysphagia to the electronic device 1000 and/or the external server through the communication module 2800, and may receive an audio signal from the electronic device 1000 and/or the external server.

The control module 2900 may control the overall operation of the audio analysis unit 2000. For example, the control module 2900 may load and execute the preprocessing module 2100, the feature extraction module 2200, the signal analysis module 2300, and programs related thereto, whereby dysphagia information may be generated from the audio signal. The control module 2900 may be implemented as a central processing unit (CPU) or a device similar to a CPU according to hardware, software, or a combination thereof. In hardware, the control module may be provided in a form of an electronic circuit configured to perform a control function by processing electrical signals, and in software, the control module may be provided in a form of a program or code for driving a hardware circuit.

The audio analysis unit 2000 may further include a memory for storing various types of information. Various data may be temporarily or semi-permanently stored in the memory. Examples of the memory may include a hard disk drive (HDD), a solid state drive (SSD), a flash memory, a read-only memory (ROM), a random access memory (RAM), etc. The memory may be provided in a form embedded in the audio analysis unit 2000 or in a detachable form.

[Audio Analysis Method]

Hereinafter, an audio analysis method performed by respective audio analysis unit 2000 will be described with reference to FIGS. 3 to 7.

According to the exemplary embodiment of the present disclosure, an audio analysis method may be divided into a process of obtaining a target signal to be analyzed and a process of analyzing the target signal. Hereinafter, each process will be first described.

Figure 3:
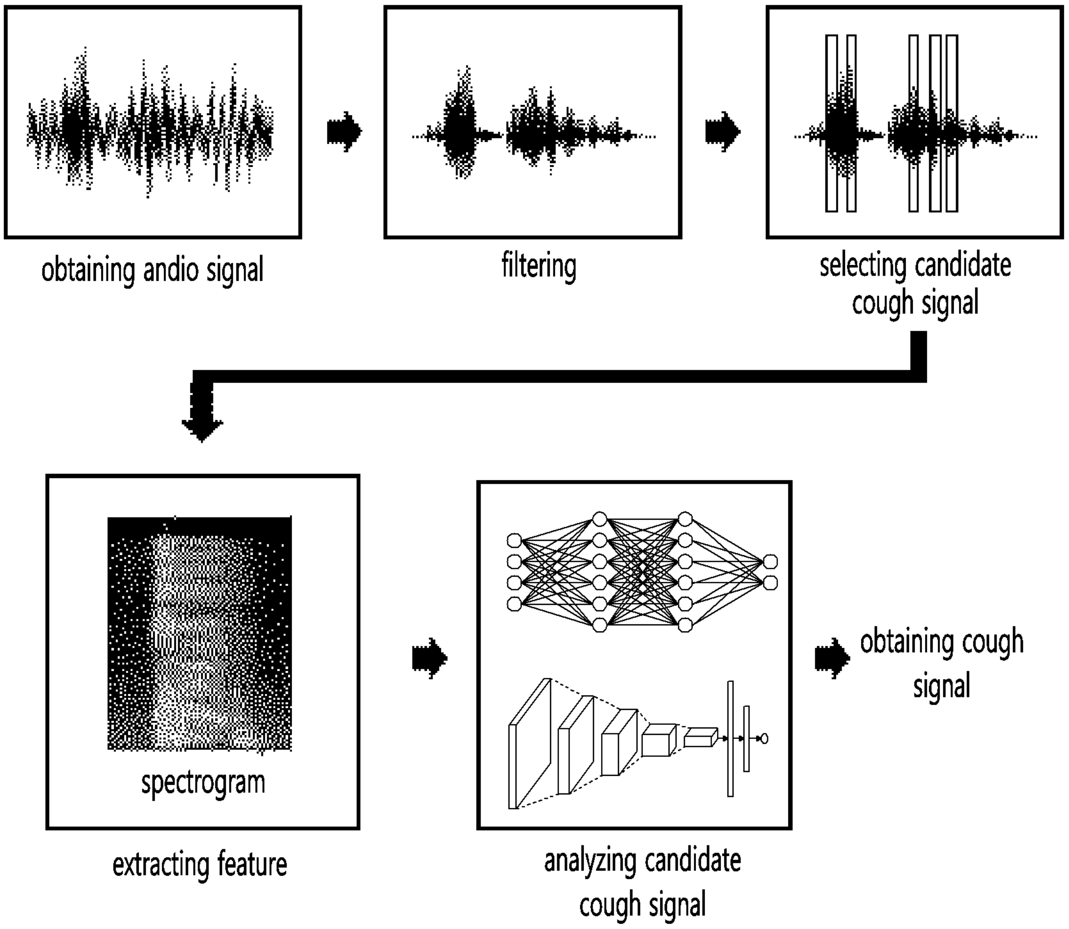
FIG. 3 is a view illustrating a process of obtaining a cough signal in an audio analysis method according to the exemplary embodiment of the present disclosure.

FIG. 3 is a view illustrating a process of obtaining a cough signal among the audio analysis method according to the exemplary embodiment of the present disclosure. Referring to FIG. 3, the process of obtaining the target signal may be divided into a process of obtaining an audio signal, a process of filtering, a process of selecting candidate cough signals, a process of extracting a feature, a process of analyzing candidate cough signals, and a process of obtaining cough signal.

An electronic device 1000 may obtain an audio signal by recording ambient sounds. Here, the recorded sounds may include sounds generated in a user's daily life, such as eating food, exercising, or performing work.

An audio analysis unit 2000 may receive the audio signal from the electronic device 1000.

A preprocessing module 2100 of the audio analysis unit 2000 may filter the audio signal. For example, the preprocessing module 2100 may apply a high-pass filter, a low-pass filter, and/or a band-pass filter in order to remove noise from the audio signal. For another example, the preprocessing module 2100 may extract only signal in a specific frequency band from the audio signal.

A candidate signal selection model 2310 of the audio analysis unit 2000 may obtain a signal satisfying a preset condition in the filtered audio signal as a candidate cough signal. For example, the candidate signal selection model 2310 may detect an onset point in the filtered audio signal, and select, as the candidate cough signal, a signal corresponding to a time section including a time point at which the onset point is detected and having a preset time interval in the filtered audio signal.

The candidate cough signal refer to a signal questioned to be a cough signal. Since one of features of the cough signal is that a magnitude of the signal increase rapidly, the signal including the above-described onset signal may be selected as the candidate cough signal.

The candidate signal selection model 2310 may select a plurality of candidate cough signals from the audio signal.

Meanwhile, the process of selecting the candidate cough signal may proceed prior to the process of filtering, and in this case, the candidate signal selection model 2310 may select the candidate cough signal from the audio signal and filtering may be performed on the selected candidate cough signal.

A feature extraction module 2200 of the audio analysis unit 2000 may extract a feature value from the candidate cough signal. Here, the feature value may be the value listed in the feature extraction module 2200, but in particular, the spectrogram magnitude value may be used therefor.

For example, in a case where the spectrogram magnitude value is used as the feature value, the feature extraction module 2200 may first convert the candidate cough signal into spectrum data including magnitude values depending on frequency. The spectrum data may be obtained by using Fourier transform (FT), fast Fourier transform (FFT), discrete Fourier transform (DFT), and short time Fourier transform (STFT). Thereafter, the feature extraction module 2200 may obtain a spectrogram image from the spectrum data. The spectrum image may be a Mel-spectrogram image to which a Mel-scale is applied.

A target signal selection model 2320 of the audio analysis unit 2000 may determine whether the candidate cough signal is a cough-related signal by using the feature value of the candidate cough signal.

As an example, the target signal selection model 2320 may receive input of a spectrogram image of the candidate cough signal and output a value indicating whether it is a cough or not. In this case, the target signal selection model 2320 may be implemented by using a deep learning model, in particular, a convolution neural network (CNN) model. Specifically, the target signal selection model 2320 may be trained to receive input of a spectrogram image and output a value indicating either a cough or a non-cough. To this end, the target signal selection model 2320 may be trained with various training data sets. Here, the training data sets may include at least a cough training data set including a spectrogram obtained by converting an audio signal recording a cough and a value indicating a cough; and a non-cough training data set including a spectrogram obtained by converting an audio signal recording sounds other than a cough and a value indicating a non-cough.

In the above, the case of using the spectrogram is mainly described in determining whether the candidate cough signal is the cough-related signal or not, but the technical idea of the present disclosure is not limited thereto. Rather, not only may other feature values be used in addition to the spectrogram, but furthermore, a cough determination method using other deep learning models in addition to the CNN model, or a cough determination method not using the deep learning model may also be used.

The audio analysis unit 2000 may obtain a signal identified as a cough among the candidate cough signals as a cough signal. Here, the cough signal may mean no other than a target signal to be analyzed. However, the target signal is not necessarily the cough signal, and may also be an audio signal related to other types of sounds (e.g., a sound of sneezing, a sound of cough by aspiration, a sound of clearing throat, a sound of dry cough, etc.). In those cases as well, the corresponding types of sounds may be detected from the audio signal by using the above-described method.

Figure 4:
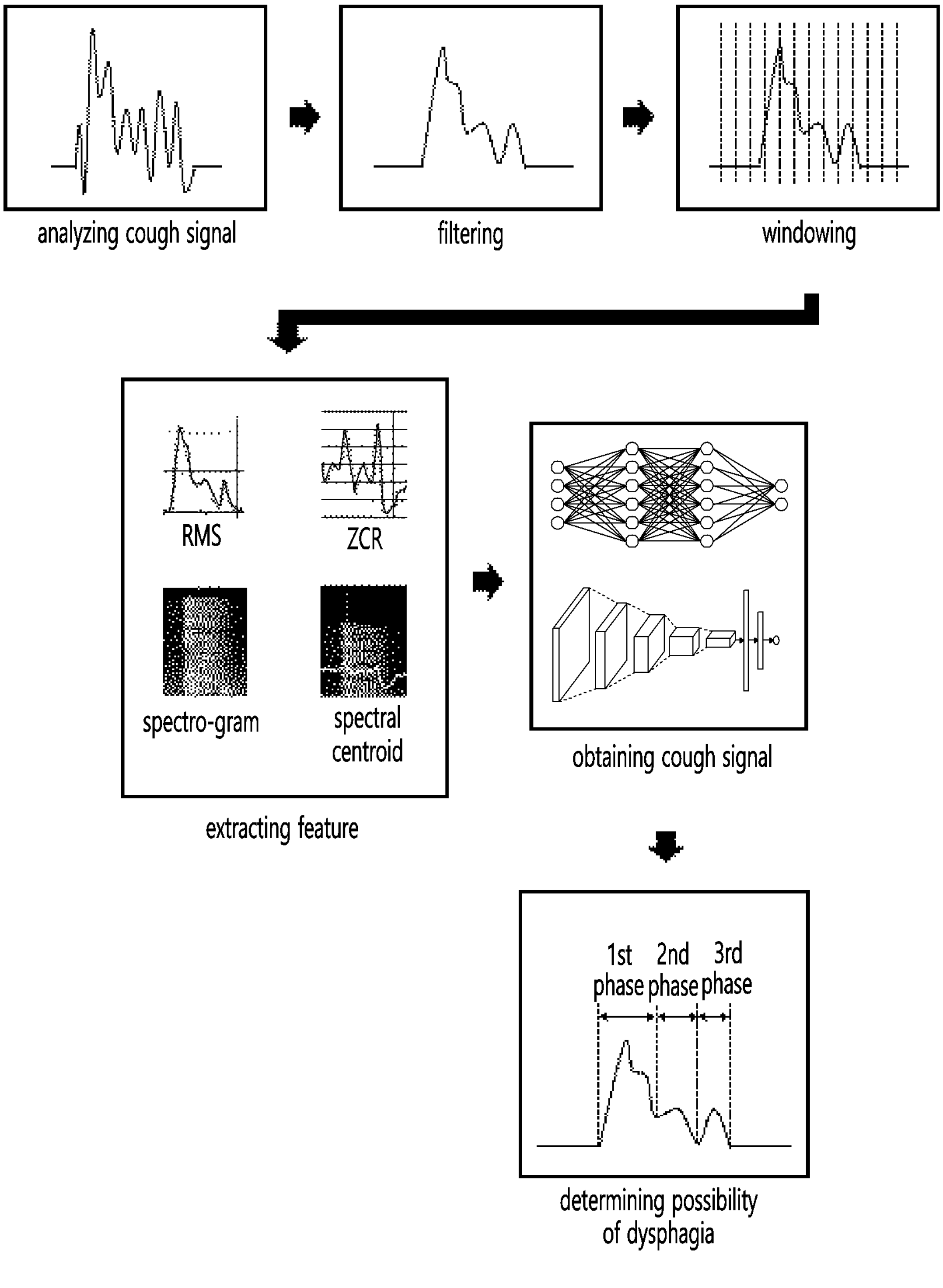
FIG. 4 is a view illustrating a process of determining a possibility of dysphagia in the audio analysis method according to the exemplary embodiment of the present disclosure.

FIG. 4 is a view illustrating a process of determining a possibility of dysphagia in the audio analysis method according to the exemplary embodiment of the present disclosure. Referring to FIG. 4, the process of determining the possibility of dysphagia may be divided into a process of obtaining a cough signal, a process of filtering, a process of windowing, a process of extracting a feature, a process of analyzing the cough signal, and a process of determining a possibility of dysphagia.

The audio analysis unit 2000 may obtain a cough signal. Here, the cough signal may be understood as a target signal to be analyzed, and it is stated in advance that as described above, the target signal may be a signal related to other types of sounds in addition to the cough signal, and even in those cases, a target signal analysis process described later may be applicable thereto.

The cough signal may be a cough signal included in any audio signal. In this case, the cough signal may be obtained through the target signal obtainment process described above.

Meanwhile, the cough signal may also be a signal obtained by recording voluntary coughing of a user. In this case, the audio signal obtained from the electronic device 1000 become no other than the cough signal, and the target signal obtainment process for obtaining the cough signal from the audio signal may be omitted.

A preprocessing module 2100 of the audio analysis unit 2000 may filter a cough signal. As being the same as that described in the process of filtering of the target signal obtainment process, the content of filtering method will be omitted.

Meanwhile, in a case where the cough signal has already been filtered in the target signal obtainment process, the process of filtering may be omitted in the target signal analysis process.

The preprocessing module 2100 of the audio analysis unit 2000 may divide the cough signal or filtered cough signal into a plurality of windows. Specifically, the preprocessing module 2100 may divide the cough signal or filtered cough signal into windows having a preset length so as to obtain fragment cough signals corresponding to respective windows.

Here, a window may mean a unit for dividing a signal. Each window may have a preset length and be determined sequentially between start point and end point of the signal.

A length of window may be determined within a preset range. For example, the length of window may be determined within 0.05 to 0.1 seconds.

The length of window may be determined in consideration of the total length of a target signal or audio signal. For example, the length of window may also be determined as a specific proportion of the total length of the target signal. For example, the length of window may be determined within 2% to 20% of the total length of a cough signal. As another example, a length of window may also be determined as a specific proportion of the total length of an audio signal being recorded.

Consecutive windows may or may not overlap each other. In a case where the consecutive windows overlap each other, the extent of overlap of the consecutive windows may be determined within 0% to 95% of a length of window. The extent of overlap of the consecutive windows may particularly be 50% of the length of window.

As an example, the preprocessing module 2100 may divide a cough signal by using windows each having a time length of 0.05 seconds and the extent of overlap of 0.01 seconds, and may obtain fragment cough signals corresponding to the respective windows. At this time, in a case where a length of a cough signal is 0.5 seconds, the number of windows dividing the cough signal is about 12, and the preprocessing module 2100 may obtain first to twelfth fragment cough signals.

The process of windowing may be understood as a process for fragmenting a cough signal into a plurality of signals. In general, rather than analyzing an audio signal as a whole, each fragmented audio signal is analyzed independently and then the results thereof are integrated so as to derive an analysis result for the entire audio signal, and thus the process of windowing is one of essential processes.

However, a case of analyzing an audio signal as a whole is also possible, and in this case, the process of windowing may be omitted. For example, in a case where a dysphagia possibility determination model 2340, which will be described below, receives input of a cough signal without fragmenting it and outputs a result thereof, the process of windowing may be omitted.

A feature extraction module 2200 may extract a feature value from the cough signal or the preprocessed cough signal. As being the same as that described in the target signal obtainment process, the content of extracting the feature value will be omitted.

Meanwhile, an RMS value, a ZCR, a spectrogram, and/or a spectral centroid may be used as the feature value in the target signal analysis process.

Before describing the cough signal analysis process, phases of a cough signal will first be described with reference to FIGS. 5A and 5B.

Below, the phases of the cough signal are described with reference to FIGS. 5A and 5B.

Figure 5A:
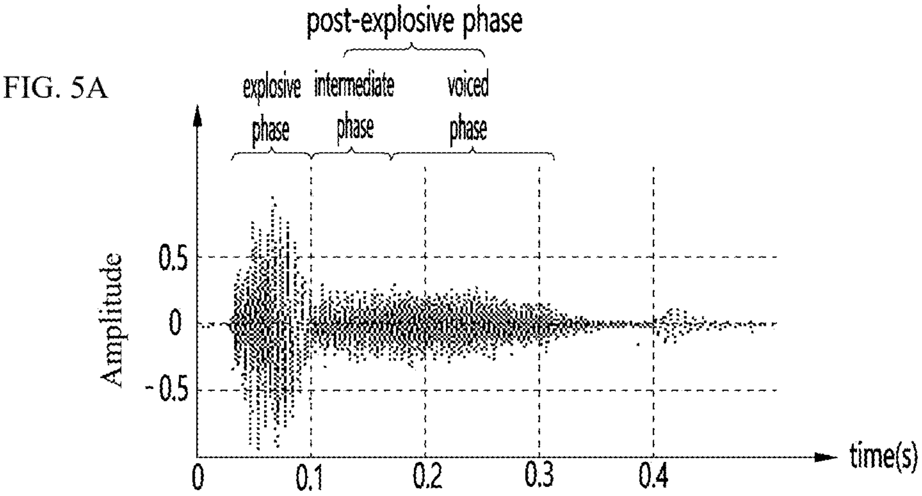
FIGS. 5A and 5B are views illustrating a normal cough signal and a dysphagia cough signal according to the exemplary embodiment of the present disclosure.
Figure 5B:
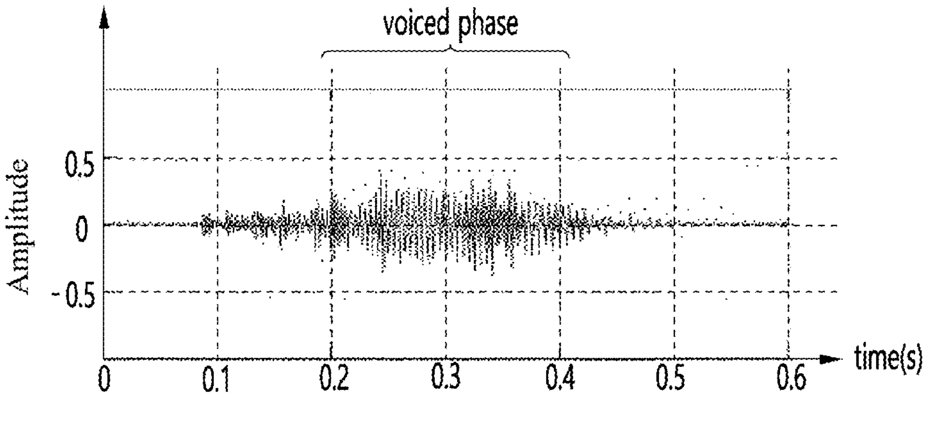

FIGS. 5A and 5B is a view illustrating a normal cough signal and a dysphagia cough signal according to the exemplary embodiment of the present disclosure.

A cough signal may be divided into a plurality of phases depending on a feature of the signal. For example, referring to FIG. 5A, the cough signal is largely divided into an explosive phase, a post-explosive phase, and then, the post-explosive phase is further divided into an intermediate phase and a voiced phase.

The explosive phase is a section corresponding to a sound which is generated as the glottis of a person closes and momentarily opens when the person coughs. Since the explosive phase is the section corresponding to the sound generated in a state where the glottis is opened, voice features are rarely present due to vocal cord tremors, but a signal tend to be generated across the entire frequency band.

The explosive phase is a beginning portion of a cough signal, and may mean a section from a start point to about 0.03 to 0.10 seconds.

In the explosive phase, the cough signal includes a signal of a relatively high frequency band. For example, when the overall frequency band of the cough signal is about 20 Hz to 16 kHz (or a frequency band of 20 Hz or more), the signal of the explosive phase may have a frequency band of about 2 kHz to 16 kHz (or a frequency band of 2 kHz or more).

A post-explosive phase refers to a section after the explosive phase for the person. Specifically, an intermediate phase of the post-explosive phase corresponds to a sound generated in a process of closing the opened glottis, and a voiced phase of the post-explosive phase corresponds to a sound generated by the vocal cords vibrating as the glottis closes.

A signal in the post-explosive phase has a feature similar to those of human voice. For example, the signal in the post-explosive phase is observed in a form of harmonic overtones in a frequency band. But in contrast, a signal in the explosive phase does not have a feature similar to those of the human voice, so harmonic overtones are not easily observed as in the post-explosive phase.

A cough signal has a relatively low frequency band in the post-explosive phase. For example, when the overall frequency band of the cough signal is about 20 Hz to 16 kHz, the signal may appear mainly in a frequency band of about 20 Hz to 4 kHz in the post-explosive phase.

FIG. 5A shows a normal cough signal of a person not suffering from dysphagia, and FIG. 5B shows a dysphagia cough signal of a person suffering from dysphagia.

Referring to FIGS. 5A and 5B, it may be confirmed that all the explosive phase, intermediate phase, and voiced phase are present in the normal cough signal whereas only the voiced phase exists in the dysphagia cough signal without an explosive phase.

This is because, in the case of the person suffering from dysphagia, a cough is not explosive but weak and a feature thereof are similar to those of human voice. Specifically, in order for an explosive phase to appear in the cough, the larynx and vocal cords are required to be suddenly opened in a state where the airway is temporarily and completely closed after filling the lungs with air. However, in the case of the patient suffering from dysphagia, making of such movements is difficult due to neurological problems or abnormalities in related organs. In particular, in a case of a patient suffering from dysphagia, the function of the laryngeal flap (or the organs surrounding the larynx, including the laryngeal flap) which opens and closes the airway is weakened, so this may be one of the main causes why a dysphagic cough signal has the aforementioned waveforms.

A signal analysis module 2300 of the audio analysis unit 2000 may obtain information for determining a possibility of dysphagia by using a feature value extracted from a cough signal.

As an example, a phase classification model2330 of the signal analysis module 2300 may divide a cough signal into at least one section. Specifically, the phase classification model 2330 may distinguish an explosive phase in the cough signal. Alternatively, the phase classification model 2330 may divide the cough signal into an explosive phase and a post-explosive phase. Alternatively, the phase classification model 2330 may divide the cough signal into an explosive phase, an intermediate phase, and a voiced phase. Alternatively, the phase classification model 2330 may divide the cough signal into an intermediate phase and a voiced phase. Alternatively, the phase classification model 2330 may distinguish a voiced phase in the cough signal.

As another example, the phase classification model 2330 may also determine whether a specific phase exists or not in a cough signal. Specifically, the phase classification model 2330 may determine whether an explosive phase exists or not in the cough signal. Alternatively, the phase classification model 2330 may determine whether a post-explosive phase exists or not in the cough signal. Alternatively, the phase classification model 2330 may determine whether a voiced phase exists or not in the cough signal.

As a yet another example, the phase classification model 2330 may provide information on an intensity of a specific phase in a cough signal. Specifically, the phase classification model 2330 may provide information on whether the intensity of an explosive phase in the cough signal is strong or weak on the basis of an average intensity (e.g., an average value, a median value, or the like of the intensity of the explosive phase in a general cough signal). Alternatively, the phase classification model 2330 may provide information on whether the intensity of a voiced phase in the cough signal is strong or weak on the basis of an average intensity (e.g., an average value, a median value, or the like of the intensity of the voiced phase in a general cough signal).

The phase classification model2330 may be implemented by using a deep learning model. The phase classification model2330 may be trained with various training data sets.

For example, the training data sets for training the phase classification model 2330 may include a first phase training data set including a first cough signal and data indicating an explosive phase in the first cough signal.

For another example, the training data sets may include a second cough signal, data indicating an explosive phase in the second cough signal, and data indicating a post-explosive phase in the second cough signal.

For a yet another example, the training data sets may include a third cough signal, data indicating an explosive phase in the third cough signal, data indicating an intermediate phase in the third cough signal, and data indicating a voiced phase in the third cough signal.

As a still another example, the phase classification model 2330 may be trained with at least a first training data set and a second training data set. Here, the first training data set may include a normal cough signal and data indicating that an explosive phase exists in the normal cough signal, and the second training data set may include a dysphagia cough signal and data indicating that an explosive phase is not present in the dysphagia cough signal.

As a still another example, the phase classification model 2330 may be trained with at least a third training data set and a fourth training data set. Here, the third training data set may include a normal cough signal and data indicating that an explosive phase is strong in the normal cough signal, and the fourth training data set may include a dysphagia cough signal and data indicating that an explosive phase is weak in the dysphagia cough signal.

A normal cough signal and a dysphagia cough signal, which are used for model learning may have the above-described feature. For example, a frequency band of a signal corresponding to a preset time period from a start point in a normal cough signal may be higher than a frequency band of a signal corresponding to a preset time period from a start point in a dysphagia cough signal. The fact that the frequency band of any one signal is higher than that of another signal may mean that a range of the frequency band, a frequency center value of the frequency band, and/or a frequency range including approximately 70% or more of the signal based on the frequency center value of any one signal are higher than those of another signal.

The form of data output from the phase classification model2330 may vary depending on training data sets with which the phase classification model 2330 is trained.

In determining whether a cough signal includes a specific phase, the phase classification model 2330 may use a commercially available program. For example, the phase classification model 2330 may determine whether a cough signal has a voiced phase, or may select a portion corresponding to a voiced phase in a cough signal by using open source or an open library configured to determine whether a random signal includes a human voice or not.

The phase classification model 2330 may divide a cough signal into at least one section on the basis of a frequency band.

For example, the phase classification model2330 may classify a signal in a relatively high frequency band (e.g., about 2 kHz to 16 kHz) as an explosive phase in a cough signal, and classify a signal in a relatively low frequency band (e.g., about 20 Hz to 4 kHz) as a post-explosive phase.

For another example, when a signal from a start point to a first time point of a cough signal in a time domain is referred to as a first signal, the phase classification model 2330 may select the first time point as a point for dividing an explosive phase and a post-explosive phase from each other in a case where an energy of the first signal compared to an energy of the entire cough signal in a frequency domain is greater than or equal to a preset first energy threshold.

For a yet another example, when a signal from a second time point to an end point of a cough signal in a time domain is referred to as a second signal, the phase classification model2330 may select the second time point as a point for dividing an explosive phase and a post-explosive phase from each other in a case where an energy of the second signal compared to an energy of the entire cough signal in a frequency domain is less than or equal to a preset second energy threshold.

The phase classification model 2330 may divide a cough signal into at least one section on the basis of a time band.

For example, the phase classification model 2330 may select a section from a start point to a third time point as an explosive phase in a cough signal. In this case, the third time point may be determined within about 0.03 to 0.10 seconds. Here, the phase classification model 2330 may also select a section from a third time point to an end point as a post-explosive phase in the cough signal.

Meanwhile, the audio analysis unit 2000 may also distinguish a specific section in a cough signal by receiving an external input. For example, the phase classification model 2330 may divide a cough signal into the above-described sections or extract a specific section from the cough signal by outputting a waveform of the cough signal as an image of a time band, a frequency band, or the like and receiving an input indicating a specific time section or frequency section in the cough signal.

The signal analysis module 2300 of the audio analysis unit 2000 may determine the presence or absence of dysphagia, the severity of dysphagia, the possibility of dysphagia, or the like by using information obtained through cough signal analysis.

First, a dysphagia possibility determination model 2340 may use feature values in each section of a cough signal.

For example, in a case where an explosive phase is not present in a cough signal or a weak explosive phase exists in a cough signal, it may be determined that a user is suffering from dysphagia or has a high possibility of suffering from dysphagia.

When an RMS value of a first signal classified into an explosive phase in the cough signal is less than or equal to a preset value, it may be determined that there is no explosive phase or a weak explosive phase exists in the cough signal.

Alternatively, when an RMS value of a first signal classified into an explosive phase in the cough signal compared to an RMS value of the entire cough signal is less than or equal to a preset value, it may be determined that there is no explosive phase or a weak explosive phase exists in the cough signal.

Alternatively, when an energy value (e.g., a square measure of a base area in a spectrum of a time domain or frequency domain) of a first signal classified into an explosive phase in a cough signal is less than or equal to a preset value, it may be determined that there is no explosive phase or a weak explosive phase exists in the cough signal.

Alternatively, when an energy value of a first signal classified into an explosive phase in a cough signal compared to an energy value of the entire cough signal is less than or equal to a preset value, it may be determined that there is no explosive phase or a weak explosive phase exists in the cough signal.

Here, it may be determined that in the cough signal, as the RMS value of the first signal classified into the explosive phase, the RMS value of the first signal which is compared to the RMS value of the entire cough signal, the energy value of the first signal, and/or the energy value of the first signal which is compared to the total energy value of the cough signal become smaller, the severity of dysphagia suffered by a user becomes greater.

As another example, in a case where a voiced phase is dominant in a cough signal, it may be determined that a user is suffering from dysphagia or has a high possibility of suffering from dysphagia.

When a ratio of a length of a second signal classified as a voiced phase in a cough signal to a length of the entire cough signal is greater than or equal to a preset ratio, it may be determined that the voiced phase is dominant in the cough signal.

As a yet another example, in a case where a post-explosive phase is dominant in a cough signal, it may be determined that a user is suffering from dysphagia or has a high possibility of suffering from dysphagia.

When a ratio of a length of a third signal classified as a post-explosive phase in a cough signal to a length of the entire cough signal is greater than or equal to a preset ratio, it may be determined that the post-explosive phase is dominant in the cough signal.

Meanwhile, the above-described section classification process for the cough signal is not an essential process in the audio analysis method. For example, the signal analysis module 2300 may analyze a cough signal to obtain feature information of the cough signal, and determine a possibility of dysphagia on the basis of the obtained feature information.

Here, the feature information may mean information on magnitudes or variance of feature values extracted from the cough signal, tendencies over time, etc.

FIGS. 6A, 6B, 7A, and 7B are views illustrating graphs for comparing features of a normal cough signal and a dysphagia cough signal according to the exemplary embodiment of the present disclosure.

Figure 6A:
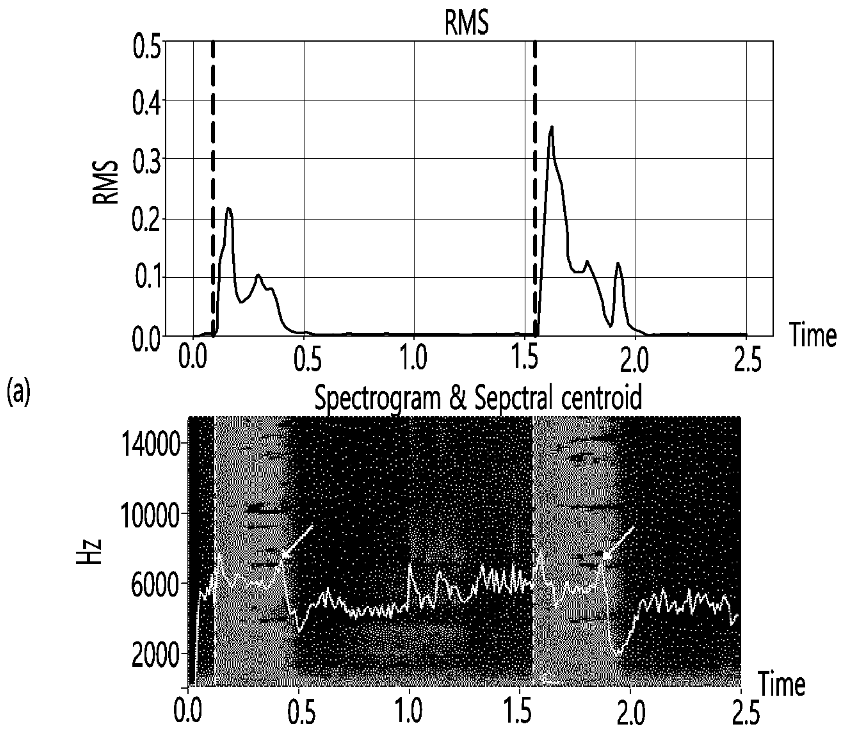
FIGS. 6A, 6B, 7A and 7B are views illustrating graphs for comparing features of a normal cough signal and a dysphagia cough signal according to the exemplary embodiment of the present disclosure.
Figure 6B:
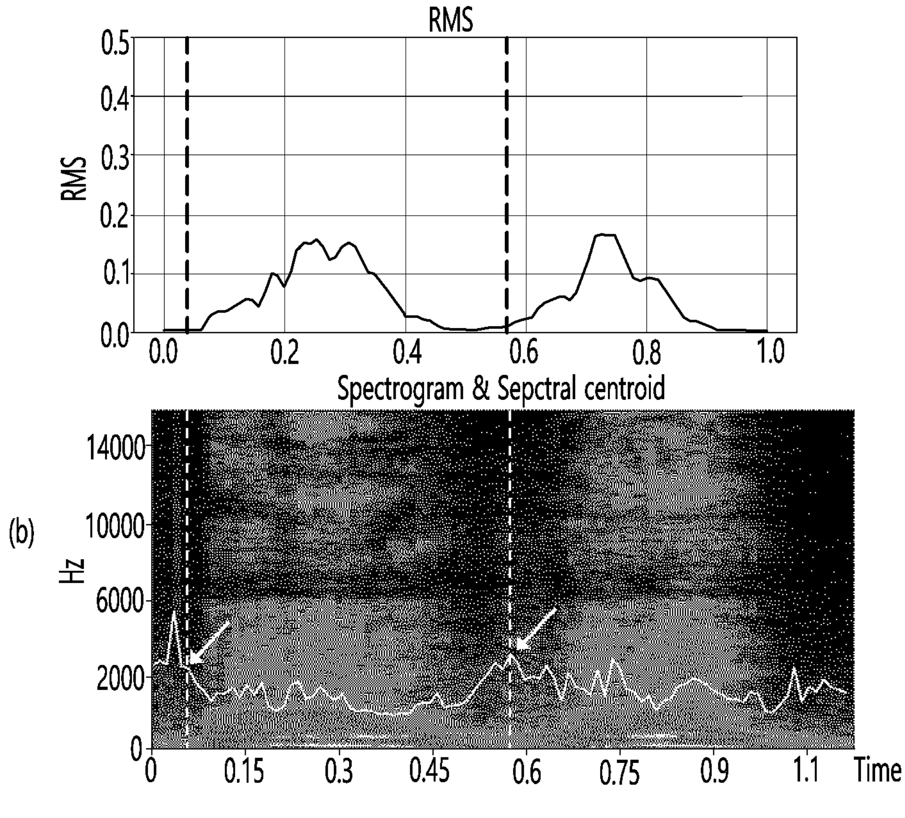

Referring to FIGS. 6A and 6B, a spectral centroid of a normal cough signal and a spectral centroid of a dysphagia cough signal may have different tendencies.

First, a spectral centroid indicates where the center of mass of a spectrum is located. The spectral centroid has a strong correlation with brightness of a sound. The spectral centroid may be understood that the higher a frequency band of a signal, the larger a spectral centroid becomes, and the lower a frequency band of the signal, the smaller the spectral centroid becomes.

Referring to FIG. 6A, in a cough signal, an explosive phase has a relatively high frequency band, and a voiced phase (or a post-explosive phase) has a relatively low frequency band, so a spectral centroid of the post-explosive phase is higher than a spectral centroid of the voiced phase.

A normal cough signal transits from an explosive phase to a voiced phase over time, thereby including a portion where the spectral centroid is lowered (i.e., a portion indicated by an arrow in FIG. 6A. More specifically, in the normal cough signal, the spectral centroid has a tendency of increasing at a start point and decreasing near an end point.

As described above, a cough of a person suffering from dysphagia has a relatively strong or dominant voiced phase. As described above, the spectral centroid of the voiced phase is relatively low, a proportion of the explosive phase is low, and a proportion of the voiced phase is high in dysphagic cough, so as shown in FIG. 6B, it may be observable that a portion (i.e., a portion indicated by an arrow in FIG. 6B) where the spectral centroid is lowered at a beginning portion of the cough signal.

In other words, in the case of the dysphagia cough signal, the explosive phase is weak and the voiced phase appears throughout the cough signal, so the spectral centroid tends to be lowered from the start point of the signal.

As a result, when a point where a spectral centroid becomes smaller exists within a preset time period from a start point of a cough signal, it may be determined that a user is suffering from dysphagia or has a high possibility of suffering from dysphagia.

However, when the strength of a cough signal itself is weak, a tendency for a spectral centroid to be lowered in the beginning of the signal may not be noticeable, so the tendency for the spectral centroid of the cough signal is required to be used rather in an auxiliary manner in determining a possibility of dysphagia.

A dysphagia possibility determination model 2340 may determine a possibility of dysphagia by using a spectrogram of a cough signal.

For example, the dysphagia possibility determination model 2340 may be implemented by a deep learning model and be trained to receive input of a spectrogram image of a cough signal and output a determination value regarding a possibility of dysphagia. Specifically, the dysphagia possibility determination model 2340 may be trained by using at least a first training data set in which a spectrogram image of a normal cough signal is labeled (or annotated) with a value indicating an absence of dysphagia; and a second training data set in which a spectrogram image of a dysphagia cough signal is labeled with a value indicating a presence of dysphagia.

Figure 7A:
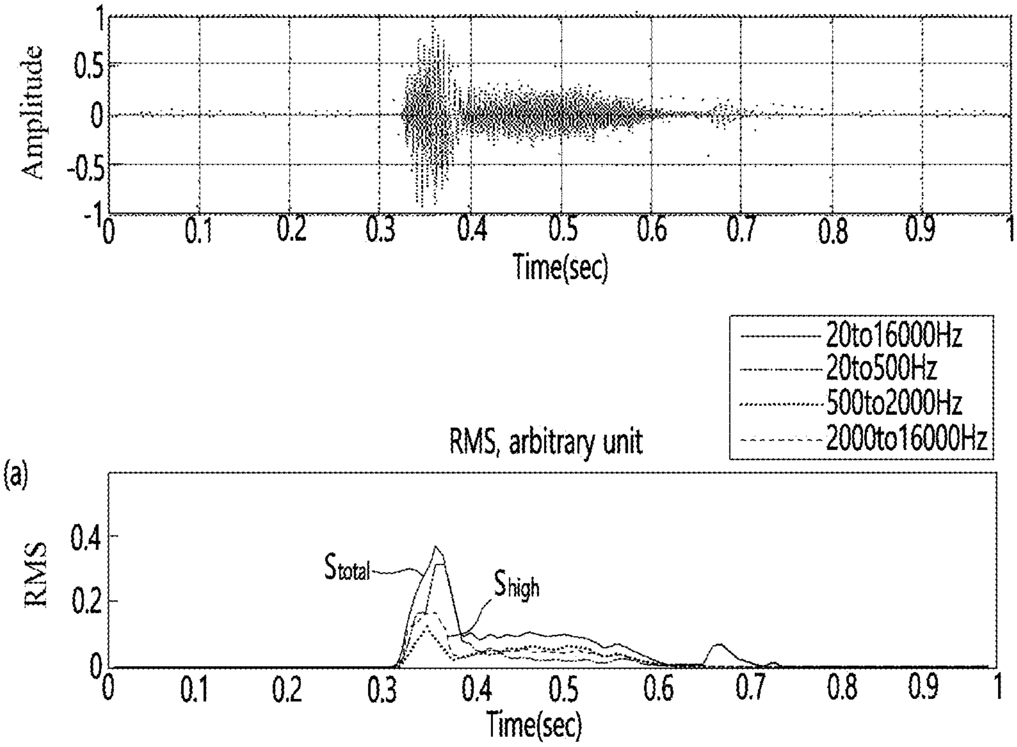
Figure 7B:
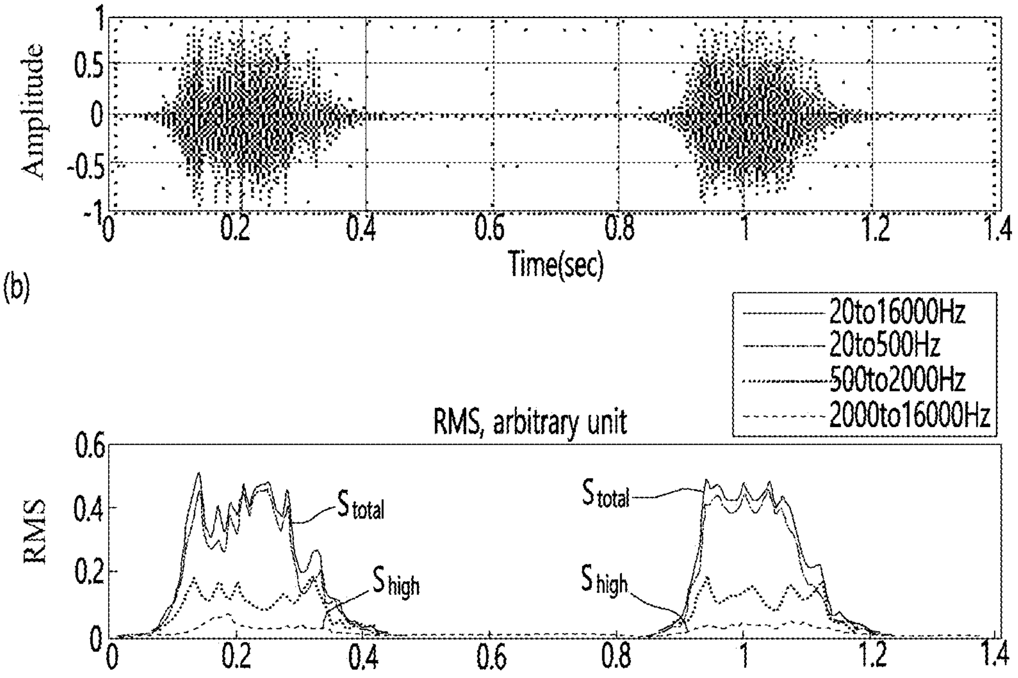

FIGS. 7A and 7B show a feature of RMS value of a normal cough signal and feature of RMS value of a dysphagia cough signal as a graph over time. More specifically, in each of the normal cough signal and the dysphagia cough signal, FIGS. 7A and 7B graphically show RMS values of the entire frequency band (e.g., 20 Hz to 16 kHz), RMS values of a first partial frequency band (e.g., 20 Hz to 500 Hz), RMS values of a second partial frequency band (e.g., 500 Hz to 2 kHz), and RMS values of a third partial frequency band (e.g., 2 kHz to 16 kHz).

Referring to FIGS. 7A and 7B, the RMS values of the normal cough signal and the RMS values of the dysphagia cough signal may have different tendencies.

Referring to FIG. 7A, in the normal cough signal, a ratio of the RMS value of the third partial frequency band (S_high) to the RMS value of the entire frequency band (S_total) has a value greater than or equal to a predetermined size. Specifically, the ratio of the RMS value of the third partial frequency band (S_high) to the RMS value of the entire frequency band (S_total) has a value of about 0.2 or more.

In contrast, referring to FIG. 7B, in the dysphagia cough signal, a ratio of the RMS value of the third partial frequency band (S_high) to the RMS value of the entire frequency band (S_total) has a value less than or equal to a predetermined size. Specifically, the ratio of the RMS values of the third partial frequency band (S_high) to the RMS values of the entire frequency band (S_total) has a value nearly close to zero.

The possibility of dysphagia may be determined on the basis of the feature of RMS value of the normal cough signal and the feature of RMS value of the dysphagia cough signal. For example, in a case where a ratio of the RMS value of the entire frequency band of a user's cough signal to be analyzed compared to the RMS value of a specific frequency band (e.g., 2 kHz to 16 kHz) is less than or equal to a predetermined value, it may be determined that the user is suffering from dysphagia.

Meanwhile, an RMS value of a cough signal for determining a possibility of dysphagia may be obtained in various ways. For example, the cough signal is divided into a plurality of fragment cough signals through the process of windowing described above, and the largest value among RMS values of the respective fragment cough signals or a value obtained by multiplying a preset multiple (e.g., 0.9) to the largest value may become an RMS value for determining the possibility of dysphagia.

Meanwhile, the method of determining the possibility of dysphagia described above may target a plurality of target signals or a plurality of cough signals as well.

For example, the dysphagia possibility determination model 2340 may determine the presence or absence of an explosive phase or a weak explosive phase for each of a plurality of target signals, and determine that there is a possibility of the dysphagia when a ratio of target signals having no explosive phase and/or target signals including weak explosive phases among the plurality of target signals is greater than or equal to a preset ratio.

For another example, the dysphagia possibility determination model 2340 may determine whether a voiced phase is dominant for a plurality of target signals, and determine that there is a possibility of the dysphagia when a ratio of target signals having the voiced phases dominant among the plurality of target signals is greater than or equal to a preset ratio.

For a yet another example, the dysphagia possibility determination model 2340 may determine whether each target signal is a signal having a possibility of dysphagia on the basis of feature information of a plurality of target signals, and determine that there is the possibility of dysphagia when a ratio of signals each having the possibility of dysphagia among the plurality of target signals is greater than or equal to a preset ratio.

[Audio Analysis Process]

Hereinafter, exemplary embodiments of the above-described audio analysis methods will be described with reference to FIGS. 8 to 12. In describing the exemplary embodiments of the audio analysis methods, a part that overlaps with the above-described content will be omitted.

Figure 8:
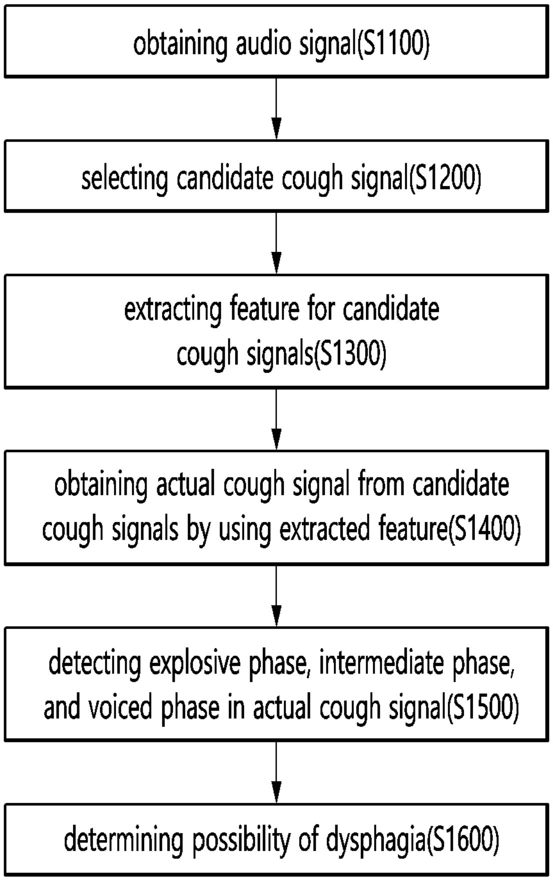
FIGS. 8 to 12 are flowcharts respectively illustrating first to fifth audio analysis methods.

FIG. 8 is a flowchart illustrating a first audio analysis method according to an exemplary embodiment of the present disclosure.

Referring to FIG. 8, the first audio analysis method may include step S1100 of obtaining an audio signal, step S1200 of selecting a candidate cough signal, step S1300 of extracting a feature for the candidate cough signals, step S1400 of obtaining an actual cough signal among the candidate cough signals by using the extracted feature, step S1500 of detecting an explosive phase, an intermediate phase, and a voiced phase from the actual cough signal, and step S1600 of determining a possibility of dysphagia.

In step S1100, an audio signals maybe obtained through an electronic device 1000. Here, the audio signal is a signal recorded around a user for a certain period of time, and may be a signal obtained by recording sounds related to actions, voices, or the like of the user.

Step S1200 of selecting a candidate cough signal may be performed by a candidate signal selection model 2310, and because of having described above, the process or method thereof will be omitted.

Step S1300 of extracting a feature for the candidate cough signals may be performed by a feature extraction module 2200, and because of having described above, the process or method thereof will be omitted.

Step S1400 of obtaining an actual cough signal from among the candidate cough signals by using the feature extracted by a target signal selection model 2320 may be performed, and because of having described above, the process or method thereof will be omitted.

Step S1500 of detecting an explosive phase, an intermediate phase, and a voiced phase in the actual cough signal may be performed by a phase classification model 2330. When the phase classification model 2330 detects a plurality of phases from the actual cough signal, a method of using the above-described deep learning model, a method of dividing the cough signal into sections according to a preset condition, and/or a method of dividing the cough signal into sections by receiving an external input may be used.

Step S1600 of determining a possibility of dysphagia may be performed by a dysphagia possibility determination model 2340. At this time, a method of determining the possibility of dysphagia through the above-described section analysis and/or a method of determining the possibility of dysphagia by using feature information of the cough signal may be used.

Figure 9:
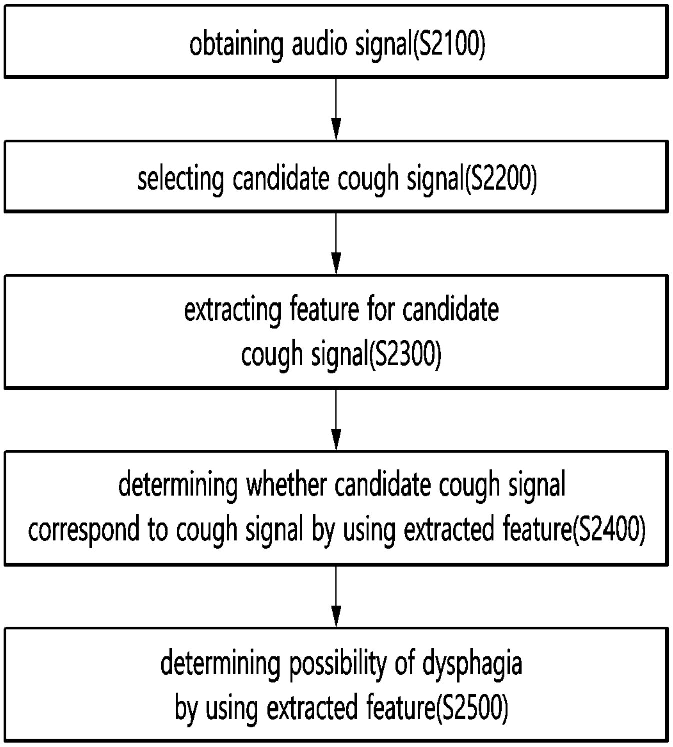

FIG. 9 is a flowchart illustrating a second audio analysis method according to an exemplary embodiment of the present disclosure.

Referring to FIG. 9, the second audio analysis method may include: step S2100 of obtaining an audio signal, step S2200 of selecting a candidate cough signal, step S2300 of extracting a feature for the candidate cough signal, step S2400 of determining whether the candidate cough signal correspond to a cough signal or not by using the extracted feature, and step S2500 of determining a possibility of dysphagia by using the extracted feature.

In the second audio analysis method, unlike the first audio analysis method, a cough signal is not divided into a plurality of phases. More specifically, step S2500 of determining a possibility of dysphagia may be performed by using the feature extracted by a dysphagia possibility determination model 2340, and in this case, a method of determining the possibility of dysphagia may be performed by using feature information on the cough signal described above.

Figure 10:
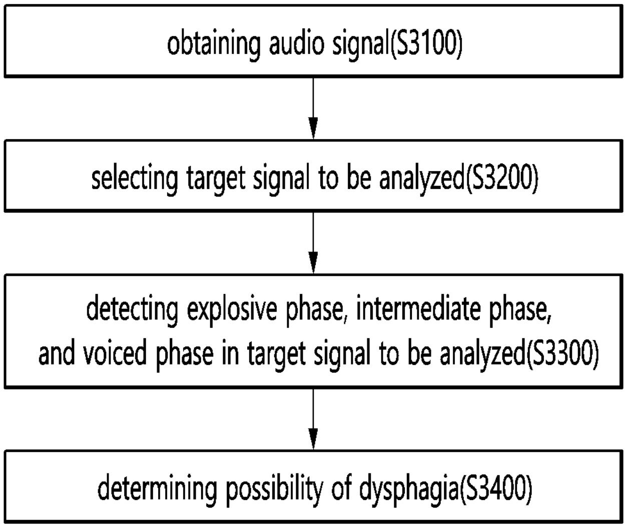

FIG. 10 is a flowchart illustrating a third audio analysis method according to an exemplary embodiment of the present disclosure.

Referring to FIG. 10, the third audio analysis method may include: step S3100 of obtaining an audio signal, step S3200 of selecting a target signal to be analyzed, step S3300 of detecting an explosive phase, an intermediate phase, and a voiced phase in target signal to be analyzed, and step S3400 of determining a possibility of dysphagia.

As being the same as that of step S1100 of obtaining the audio signal in the first audio analysis method, the description of step S3100 of obtaining the audio signal will be omitted.

Step S3200 of selecting the target signal to be analyzed may be performed by a candidate signal selection model 2310. Here, the target signal to be analyzed refer to a signal of portion to be analyzed in the audio signal, and may be similar to those of the process of selecting the candidate cough signal described above. For example, the target signal to be analyzed may be a signal corresponding to a time section including an onset point and having a preset length of the audio signal.

Step S3300 of detecting an explosive phase, an intermediate phase, and a voiced phase in each target signal to be analyzed may be performed by a phase classification model 2330. To this end, the phase classification model 2330 may use a method of dividing a specific signal into at least one or more sections by using a deep learning model.

As being the same as step S1600 of determining the possibility of dysphagia of the first audio analysis method, step S3400 of determining the possibility of dysphagia will be omitted.

Figure 11:
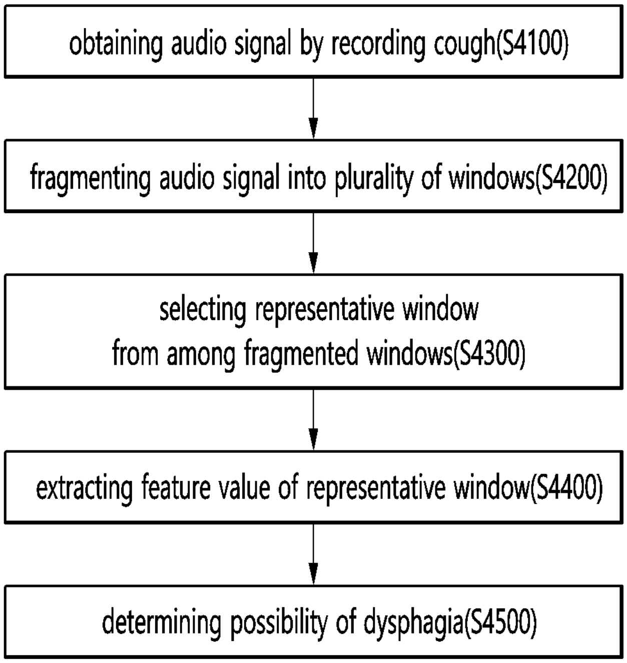

FIG. 11 is a flowchart illustrating a fourth audio analysis method according to an exemplary embodiment of the present disclosure.

Referring to FIG. 11, the fourth audio analysis method may include: step S4100 of obtaining an audio signal by recording a cough; step S4200 of fragmenting the audio signal into a plurality of windows; step S4300 of selecting a representative window from among the fragmented windows; step S4400 of extracting a feature value (i.e., an RMS value) of the representative window; and step S4500 of determining a possibility of dysphagia.

In step S4100, an audio signal obtained by recording a cough may be obtained through an electronic device 1000. Here, the audio signal obtained by recording the cough may mean a signal obtained by recording voluntary coughing of a user. The electronic device 1000 may provide a guide to induce recording voluntary coughing of the user.

Meanwhile, in a case of a person suffering from dysphagia, the intensities of coughs tends to gradually weaken when the person coughs successively. In other words, in order to more clearly determine a possibility of dysphagia, the electronic device 1000 may induce the user to cough successively (e.g., three to seven times in a row), and the audio analysis unit 2000 may analyze the user's voluntary coughs (especially the low-ranking coughs in time series).

Step S4200 of fragmenting the audio signal into a plurality of windows may be performed by a preprocessing module 2100, and as being the same as the content described in the process of windowing, description of this step will be omitted.

A dysphagia possibility determination model 2340 may perform steps including: step S4300 of selecting a representative window from among the fragmented windows; step S4400 of extracting a feature value of the representative window; and step S4500 of determining a possibility of dysphagia, and as being the same as the method of determining the possibility of dysphagia by using the RMS value, description of these steps will be omitted.

In performing the fourth audio analysis method, a candidate signal selection model 2310, target signal selection model 2320, and phase classification model 2330 of the audio analysis unit 2000 may be omitted.

Figure 12:
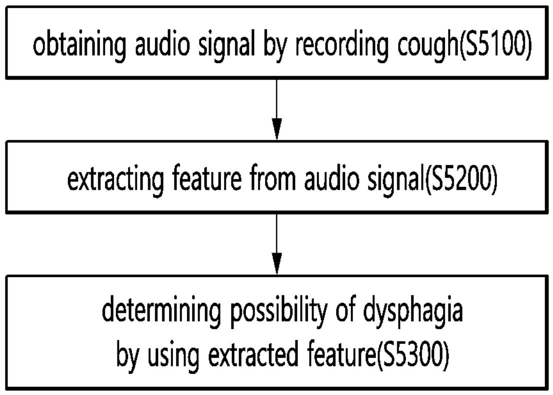

FIG. 12 is a flowchart illustrating a fifth audio analysis method according to an exemplary embodiment of the present disclosure.

Referring to FIG. 12, the fifth audio analysis method may include: step S5100 of obtaining an audio signal by recording a cough; step S5200 of extracting a feature from the audio signal; and step S5300 of determining a possibility of dysphagia by using the extracted feature.

As being the same as step S4100 of the fourth audio analysis method, description of step S5100 of obtaining the audio signal by recording the cough will be omitted.

Step S5200 of extracting the feature from the audio signal may be performed by a feature extraction module 2200, and because of having described above, the process or method thereof will be omitted.

Step S5300 of determining the possibility of dysphagia may be performed by using the feature extracted by a dysphagia possibility determination model 2340, and the method of determining the possibility of dysphagia may be applicable by using the spectrograms described above.

Similar to the fourth audio analysis method, in performing the fifth audio analysis method, a candidate signal selection model 2310, target signal selection model 2320, and phase classification model2330 of the audio analysis unit 2000 may be omitted.

Meanwhile, in determining the possibility of dysphagia, two or more of the first to fifth audio analysis methods described above may also be used.

[Monitoring Dysphagia or Emergency Situation]

Hereinafter, with reference to FIG. 13, a method of monitoring a condition of dysphagia and further detecting an emergency situation to provide a notification by using the audio analysis method described above will be described.

Figure 13:
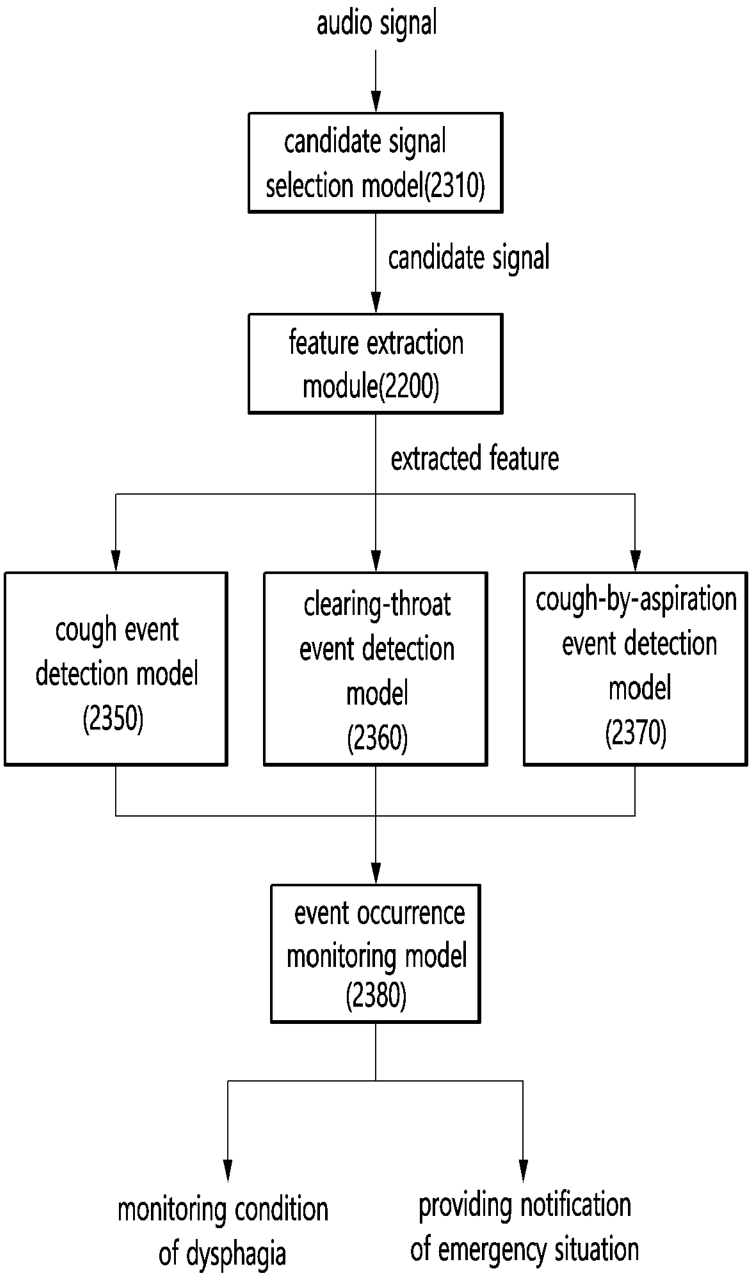
FIG. 13 is a view illustrating cases in which the audio analysis method is utilized according to the exemplary embodiment of the present disclosure.

FIG. 13 is a view illustrating a case where an audio analysis method is utilized according to the exemplary embodiment of the present disclosure. Referring to FIG. 13, the audio analysis system 10 may monitor a condition of dysphagia by using an audio signal, and provide a notification of an emergency situation.

The condition of dysphagia may mean severity or seriousness of the dysphagia suffered by a user. Monitoring the condition of dysphagia may be understood as checking whether the severity or seriousness of dysphagia has worsened or improved.

An emergency situation may mean a situation in which the user's health rapidly deteriorates or the user is in imminent danger, requiring immediate first aid. For example, the emergency situation may be considered in a case where the user coughs by aspiration or abnormally coughs a lot while eating, or vomits or suffocates due to a sudden problem with the respiratory tract.

The audio analysis system 10 may detect the presence or absence of a specific event for a given audio signal, and may monitor a condition of dysphagia or provide a notification of an emergency situation on the basis of the number of detections for each event. Hereinafter, the processes thereof are described in detail. Here, the event to be detected through the audio analysis system 10 may include an event of coughing, an event of clearing throat (or dry coughing), and an event of cough by aspiration.

First, an audio signal may be obtained by an electronic device 1000. Here, the audio signal may be related to sounds generated in daily life, such as food intake, exercise, or work performance of a user.

The candidate signal selection model 2310 may select a candidate signal from the audio signal. The process of selecting the candidate signal may be performed by using the method of detecting the onset point as described above, and because of having described above, the detailed content thereof will be omitted.

Meanwhile, a process of filtering may be performed by a preprocessing module 2100 either before the candidate signal selection process or after the candidate signal selection process.

A feature extraction module 2200 may extract a feature from the candidate signal. For example, the feature extraction module 2200 may extract a feature value such as an RMS value, spectral data (e.g., a spectrum image or a Mel spectral image, etc.), and/or a spectral centroid from the candidate signal.

The feature extraction module 2200 may extract a feature for the entire candidate signal or extract a feature for each of fragment signals obtained through a process of windowing.

A signal analysis module 2300 may determine whether the audio signal include an event of coughing, an event of clearing throat (or dry coughing), and an event of cough by aspiration on the basis of the feature extracted from the candidate signal. To this end, the signal analysis module 2300 may further include a cough event detection model 2350, a clearing-throat event detection model 2360, and an cough-by-aspiration event detection model2370.

The cough event detection model 2350, the clearing-throat event detection model 2360, and the cough-by-aspiration event detection model 2370 may be implemented identically to a target signal selection model 2320.

For example, the clearing-throat event detection model 2360 may receive a spectrogram image of a candidate signal and output a value indicating whether a signal is related to a sound of clearing throat or not. In this case, the clearing-throat event detection model 2360 may be implemented by using a deep learning model, particularly, a CNN model. Specifically, the clearing-throat event detection model 2360 may be trained to receive input of the spectrogram image and output a value indicating a sound of clearing throat or a value indicating not a sound of clearing throat. To this end, the clearing-throat event detection model 2360 may be trained with various training data sets. Here, the training data sets may include at least a first training data set including a spectrogram image obtained by converting an audio signal obtained by recording sounds of clearing throat, and a value indicating the sound of clearing throat; and a second training data set including a spectrogram image obtained by converting an audio signal obtained by recording sounds that are not sounds of clearing throat, and a value indicating not the sound of clearing throat.

In addition, the cough-by-aspiration event detection model 2370 may receive input of a spectrogram image of the candidate signal and output a value indicating whether a cough-by-aspiration signal. In this case, the cough-by-aspiration event detection model 2370 may be implemented by using a deep learning model, particularly a CNN model. Specifically, the cough-by-aspiration event detection model 2370 may be trained to receive input of a spectrogram image and output a value indicating a cough by aspiration or a value indicating not a cough by aspiration. To this end, the cough-by-aspiration event detection model 2370 may be trained with various training data sets. Here, the training data sets may include at least a first training data set including a spectrogram image obtained by converting an audio signal obtained by recording sounds of cough by aspiration, and a value indicating the sounds of the cough by aspiration; and a second training data set including a spectrogram image obtained by converting an audio signal obtained by recording sounds that are not the cough by aspiration, and a value indicating not the cough by aspiration.

Because of overlapping with what is described in the target signal selection model 2320, the description of the cough event detection model 2350 is omitted.

Meanwhile, the cough event detection model 2350, the clearing-throat event detection model2360, and the cough-by-aspiration event detection model2370 may be implemented as one model. For example, one integrated model may be trained by using at least one of training data set for coughing, a training data set for clearing throat, and a training data set for cough by aspiration, and in this case, the integrated model may receive input of an audio signal, and determine whether a cough event, a cough-by-aspiration event, or a clearing-throat event are detected or not.

The signal analysis module 2300 may further include an event occurrence monitoring model 2380.

The event occurrence monitoring model 2380 may obtain information on whether each event is detected or not from the above-described event detection models.

The event occurrence monitoring model 2380 may monitor a condition of dysphagia on the basis of the information on whether each event is detected or not.

For example, the event occurrence monitoring model 2380 may determine that a condition of dysphagia has worsened in cases including: a case where the number of cough event occurrences is greater than or equal to a first threshold value; a case where the number of clearing-throat event occurrences is greater than or equal to a second threshold value; and/or a case where the number of cough-by-aspiration event occurrences is greater than or equal to a third threshold value.

For another example, the event occurrence monitoring model 2380 may determine that a condition of dysphagia has worsened in cases including: a case where the number of cough event occurrences within a first time period is greater than or equal to a fourth threshold value; a case where the number of clearing-throat event occurrences within a second time period is greater than or equal to a fifth threshold value; and/or a case where the number of cough-by-aspiration event occurrences within a third time period is greater than or equal to a sixth threshold value.

As described above, in a case where it is determined that the condition of dysphagia have worsened as a result of analyzing the audio signal, the audio analysis unit 2000 may provide a notification through an output module 2700 or transmit information on the condition of dysphagia to the electronic device 1000 or an external server.

The event occurrence monitoring model 2380 may detect an occurrence of an emergency situation and provide a notification on the basis of the information on whether each event is detected or not.

For example, the event occurrence monitoring model 2380 may determine that a condition of dysphagia has worsened in cases including: a case where the number of cough event occurrences within a fourth time period is greater than or equal to a seventh threshold value; a case where the number of clearing-throat event occurrences within a fifth time period is greater than or equal to a eighth threshold value; and/or a case where the number of cough-by-aspiration event occurrences within a sixth time period is greater than or equal to a ninth threshold value.

As described above, in a case where it is determined that an emergency situation occurs as a result of analyzing the audio signal, the audio analysis unit 2000 may provide a notification through an output module 2700 or transmit information on the emergency situation to the electronic device 1000 or an external server. In this case, reporting of the emergency situation or requesting rescue may be automatically made by the audio analysis unit 2000.

Meanwhile, as described above, the detecting of the cough event, clearing-throat event, and cough-by-aspiration event may be performed in real time. For example, the electronic device 1000 may activate a recording function thereof so as to obtain real-time audio signal by recording a user's voices or ambient sounds in real time. The audio analysis unit 2000 may periodically analyze the real-time audio signal obtained from the electronic device 1000 so as to monitor a condition of dysphagia, or determine whether an emergency situation has occurred or not.

The exemplary embodiments according to the present disclosure described above may be implemented in the form of program instructions executable through various computer components and be recorded on a non-transitory computer-readable recording medium. The non-transitory computer-readable recording medium may include program instructions, data files, data structures, and the like individually or in combination thereof. The program instructions recorded on the computer-readable recording medium may be those specially designed and configured for the embodiments of the present disclosure, or may be known and available to those skilled in the art of computer software. Examples of the computer-readable recording media include: magnetic media such as hard disks, floppy disks, and magnetic tapes; optical media such as CD-ROMs and DVDs; magneto-optical media such as floptical disks; and a hardware device specially configured to store and execute program instructions, the hardware device including such as ROM, RAM, flash memory, etc. Examples of the program instructions include not only machine language code such as those generated by a compiler, but also high-level language code that may be executed by a computer using an interpreter or the like. The hardware device described above may be configured to operate by one or more software modules to perform processes according to the embodiments of the present disclosure, and vice versa.

In the above, features, structures, effects, etc. described in the above exemplary embodiments are included in at least one embodiment of the present disclosure, but are not necessarily limited to only one embodiment. Furthermore, the features, structures, effects, etc. illustrated in each embodiment may be implementable by way of combinations or modifications for other embodiments by those skilled in the art to which the embodiments belong. Accordingly, the contents related to such combinations and modifications should be interpreted as being included in the scope of the present disclosure.

In addition, in the above, the present disclosure has been described focusing on the embodiments, but these are only examples and do not limit the technical idea of the present disclosure, and thus those skilled in the art to which the present disclosure pertains will appreciate that various modifications and applications not exemplified above are possible without departing from the essential characteristics of the present embodiments. That is, each component specifically shown in the embodiments may be implemented by modifications. In addition, differences related to such modifications and applications should be construed as being included in the scope of the present disclosure defined in the appended claims.

The invention claimed is:

1. An audio analysis method for providing information on dysphagia, the audio analysis method comprising:

obtaining an audio signal by using an electronic device; and generating information for the dysphagia by analyzing the audio signal;

wherein the analyzing the audio signal comprises:

extracting one or more onset signals from the audio signal, wherein the one or more onset signals have a preset length;

converting each of the one or more onset signals into a spectrogram image;

determining, based on the one or more spectrogram images, one or more cough signals using a cough determination model, wherein the determined cough signals include at least one explosive cough signal including an explosive phase and at least one non-explosive cough signal not including an explosive phase;

only for the one or more cough signals:

determining whether the non-explosive cough signal exists using a phase classification model, wherein the phase classification model is trained based on a training data set, wherein the training data set comprises data corresponding to a first type cough signal comprising the explosive phase and data corresponding to a second type cough signal not comprising the explosive phase, and wherein the training data set have a characteristic that a frequency band of a signal corresponding to a preset time period from a start point of the first type cough signal in the first type cough signal is higher than a frequency band of a signal corresponding to the preset time period from a start point of the second type cough signal in the second type cough signal, wherein the generating information for the dysphagia comprises:

generating the information relating a risk of dysphagia in response to the non-explosive cough signal is exist.

2. The audio analysis method of claim 1, further comprising:

obtaining an intensity value of the explosive phase of the cough signal when the explosive phase exists in the cough signal; and determining that there is a possibility of the dysphagia when the intensity value is less than or equal to a preset value.

3. The audio analysis method of claim 1, wherein the determining of whether the non-explosive cough signal exists is performed for a plurality of cough signals, and the audio analysis method further comprises determining that there is a possibility of the dysphagia when a ratio of cough signals in which the non-explosive cough signal exists among the plurality of cough signals is greater than or equal to a preset value.

4. An audio analysis method for providing information on dysphagia, the audio analysis method comprising:

outputting a guide so as to induce voluntary coughing of a user by using an electronic device;

obtaining a audio signal by recording a sound generated by the user by using the electronic device;

generating information for the dysphagia by analyzing the audio signal;

wherein the analyzing the audio signal comprises:

extracting one or more onset signals from the audio signal, wherein the one or more onset signals have a preset length;

converting each of the one or more onset signals into a spectrogram image;

determining, based on the one or more spectrogram images, one or more cough signals using a cough determination model, wherein the determined cough signals include at least one explosive cough signal including an explosive phase and at least one non-explosive cough signal not including an explosive phase;

only for the one or more cough signals:

dividing each of the one or more cough signals into a first time section starting from a start point of the cough signal and a second time section after the first time section; and determining whether the non-explosive cough signal exists by analyzing a first signal corresponding to the first time section in the cough signal, wherein the generating information for the dysphagia comprises:

generating the information relating a risk of dysphagia in response to the non-explosive cough signal is exist.

5. The audio analysis method of claim 4, wherein the analyzing the audio signal comprises:

converting each of the one or more cough signals into a cough spectrogram image;

obtaining a root mean square (RMS) value of a specific frequency band of the cough spectrogram image; and determining that there is non-explosive cough signal when the RMS value is less than or equal to a preset value.

6. The audio analysis method of claim 4, wherein the analyzing the audio signal comprises:

converting each of the one or more cough signals into a cough spectrogram image;

obtaining a ratio of an RMS value of a specific frequency band to an RMS value of an entire frequency band of the cough spectrogram image; and determining that there is non-explosive cough signal when the ratio is less than or equal to a preset ratio value.

* * * * *